(12) United States Patent
Xue

(10) Patent No.: US 10,722,547 B2
(45) Date of Patent: Jul. 28, 2020

(54) COMPOSITIONS OF MEDICINAL PLANTS FOR REDUCING THE EFFECTS OF AGING, PREVENTION AND TREATMENT OF AGE-RELATED NEURODEGENERATIVE DISEASES, AND TREATMENT OF ANXIETY AND SLEEP DISORDERS

(71) Applicant: PharmacoGenetics Limited, Shatin, N.T. (CN)

(72) Inventor: Hong Xue, Hong Kong (CN)

(73) Assignee: PharmacoGenetics Limited, Shatin, N.T. (FR)

( * ) Notice: Subject to any disclaimer, the term of this patent is extended or adjusted under 35 U.S.C. 154(b) by 567 days.

(21) Appl. No.: 15/255,876

(22) Filed: Sep. 2, 2016

(65) Prior Publication Data
US 2018/0064773 A1 Mar. 8, 2018

(51) Int. Cl.
  A61K 36/48 (2006.01)
  A61K 36/00 (2006.01)
  A61K 36/66 (2006.01)
  A61K 36/70 (2006.01)
  A61K 36/704 (2006.01)
  A61K 36/233 (2006.01)

(52) U.S. Cl.
  CPC ............ *A61K 36/233* (2013.01); *A61K 36/48* (2013.01); *A61K 36/66* (2013.01); *A61K 36/704* (2013.01); *A61K 2236/00* (2013.01)

(58) Field of Classification Search
  None
  See application file for complete search history.

(56) References Cited

U.S. PATENT DOCUMENTS

| | | | | |
|---|---|---|---|---|
| 2011/0171329 | A1* | 7/2011 | Cheng | A61K 31/7048 424/741 |
| 2016/0004298 | A1* | 1/2016 | Mazed | G06F 3/011 345/633 |

FOREIGN PATENT DOCUMENTS

| CN | 1294002 A | 5/2001 |
|---|---|---|
| CN | 1493353 A | 5/2004 |
| CN | 1723990 A | 1/2006 |
| CN | 101653525 A | * 2/2010 |
| CN | 102210738 A | * 10/2011 |
| CN | 102743523 A | 10/2012 |
| CN | 103585429 A | 2/2014 |
| CN | 104940844 A | 9/2015 |

OTHER PUBLICATIONS

Dai, C., et al., "Study on Antioxidation Effect In Vivo of Flavonoids From Caulis Polygoni Multiflori," Journal of Shaanxi Normal University (Natural Science Edition), Jul. 2011, pp. 75-78, vol. 38, No. 4.
Du, K., et al., "Structural Analysis and Antioxidation Activity of Bupleurum Polysaccharide," Chinese Journal of Bioprocess Engineering, Jul. 2011, pp. 45-48, vol. 9, No. 4.
International Search Report and Written Opinion issued for PCT/IB2017/055279 dated Jan. 3, 2018, 15 pages.
Xu, L., et al., "Effect of Yanhusuo on Learning Capability and Anti-oxidation of Mice," Journal of Zhejiang Normal University (Nat. Sci.), Nov. 2001, pp. 374-376, vol. 24, No. 4.
Yuan, J., et al., "Study on Extraction Technology of Polysaccharides from Flos Albiziac and Its Antioxidation Activity," Hubei Agricultural Sciences, Jun. 2013, pp. 2625-2628, vol. 52, No. 11.

\* cited by examiner

*Primary Examiner* — Michael Barker
(74) *Attorney, Agent, or Firm* — Lewis Rice LLC

(57) ABSTRACT

Compositions comprising extracts prepared from mixtures of the herbal plants Radix *Bupleurum chinense* DC ("B"), Rhizoma *Corydalis yanhusuo* WT Wang ("Y"), Caulis *Polygonum multiflorum* Thunb ("P") and Flos *Albizia julibrissin* Durazz ("A") are provided. The BYP, BYA, BPA, BY, BP, YP and BYPA extracts significantly decreased one or more of the effects of accelerated aging in mice exposed to D-galactose, including spatial memory deficit, and elevated oxidative stress marker malondialdehyde and pro-inflammatory cytokines TNF-alpha and IL-6 in the brain, indicating efficacy in reducing the damage of aging, and preventing and treating Alzheimer's disease and/or Parkinson's disease. Anxiolysis by the BYA, BPA, YPA, BA and PA extracts indicates efficacy for treating anxiety disorders, and the sedative effect of the BYA, YPA and PA extracts indicates efficacy for treating sleep disorders. None of the extracts significantly induced alteration in locomotor activity, decreased muscle coordination, or anterograde amnesia at the maximum oral dose tested.

20 Claims, 5 Drawing Sheets

COMPOSITIONS OF MEDICINAL PLANTS FOR REDUCING THE EFFECTS OF AGING, PREVENTION AND TREATMENT OF AGE-RELATED NEURODEGENERATIVE DISEASES, AND TREATMENT OF ANXIETY AND SLEEP DISORDERS

FIELD OF THE INVENTION

The present invention generally relates to decoctions prepared from varying mixtures of the medicinal plants Radix *Bupleurum chinense* DC ("B"), Rhizoma *Corydalis yanhusuo* WT Wang ("Y"), Caulis *Polygonum multiflorum* Thunb ("P") and Flos *Albizia julibrissin* Durazz ("A"). More particularly, the invention relates to therapeutic agents or herbal supplements for reducing the effect of aging, prevention and treatment of age-related neurodegenerative disorders such as Alzheimer's disease (AD) and Parkinson's disease (PD), treatment of anxiety, and treatment of sleep disorders.

BACKGROUND OF THE INVENTION

The world's population is aging rapidly, and the number of people over 60 years of age will rise to 2 billion in 2050. As a result, age-related cognitive decline is becoming a pressing social and health concern. Physiologically, damage to the structures of the medial temporal lobe including the hippocampus, contributing to the decreased spatial memory often associated with aging, represents one research focus in this regard (Barnes 1988; von Bohlen and Halbach et al 2006). Biochemically, oxidative damage by reactive oxygen species (ROS) has been implicated in normal aging (Finkel and Holbrook 2000; Barja 2004). There is in the human body also a balance between pro-inflammatory agents such as interleukin-6 (IL-6), C-reactive protein and tumor necrosis factor-alpha (TNF-alpha), which can confer high resistance to infectious diseases but also increased susceptibility to inflammation-based diseases later in life, and anti-inflammatory agents such as TNF-beta and IL-10. In old age, the balance is shifted to the pro-inflammatory agents, resulting in a chronic low-grade inflammation referred to as 'inflammaging', which is accompanied by elevated pro-inflammatory cytokines, and represents a highly significant factor for both morbidity and mortality (Franceschi et al 2007; Franceschi and Campisi 2014). Long-lived people, especially centenarians, seem to cope with inflammaging through an "anti-inflammaging" cytokine response, and it is suggested that anti-inflammaging may be a key to longevity (Minciullo et al 2016). Therefore treatments that can alleviate spatial memory deficit, relieve oxidative stress and/or lower elevated levels of pro-inflammatory agents such as TNF-alpha and IL-6 are important for reducing the effect of aging.

The health problems of normal aging overlap with those posed by age-related degenerative diseases. Thus memory loss is the key affliction in Alzheimer's disease ("AD") (Wolbers et al 2014; Tanila 2012). Oxidative stress is important to both Alzheimer's disease and Parkinson's disease (Lovell et al 1995; Nunomura et al 2001; Perry et al 2002; Henchcliffe and Beal 2008), and antioxidants have been proposed for the prevention and treatment of neurodegenerative disorders including both Alzheimer's disease and Parkinson's disease (Prasad et al 1999; Moosmann and Behl 2002; Fernandez-Checa et al 2010). In addition, AD is associated with the occurrence of amyloid plaques, tau-protein abnormalities and neuroinflammation, and it has been suggested that neuroinflammation is not a passive system activated by emerging senile plaques and neurofibriller tangles, but contributes as much or more to pathogenesis as do plaques and tangles themselves (Heneka et al 2015). When 56 patients with mild cognitive impairment (MCI) were monitored prospectively for nine months, 25 patients remained at the MCI stage while the other 31 patients had progressed to AD. Only the latter group showed significantly higher cerebralspinal fluid levels of TNF-alpha than controls, indicating that CNS inflammation is an early hallmark in AD pathogenesis (Tarkowski et al 2003). Cytokine expression profiles in the brain of two transgenic mouse models of AD, viz. TgAPPsw and PS1/APPsw, also confirmed that these brains are under active inflammatory stress with major enhancement of TNF-alpha, IL-6, IL1-alpha and GM-CSF in the brain slices (Patel et al 2005). Trials to date of anti-inflammatory prevention of AD with aspirin, steroidal and non-steroidal anti-inflammatory drugs have yielded disappointing results (Jaturapatpom et al 2012; Alzheimer's Disease Anti-inflammatory Prevention Trial Reseach Group 2013) despite earlier, more positive outcomes (Breitner 2011). However, the non-steroidal anti-inflammation drug (NSAID)-derived CHF5074 reduced the concentrations of the neuroinflammation biomarkers TNF-alpha and sCD40L in the cerebrospinal fluid of patients with mild cognitive impairment (Ross et al 2016). Such modulation of neuroinflammation markers supports the suggestion that combination therapy consisting of a drug targeting the amyloid-beta (Aβ) and/or tau protein, and a medication modulating neuroinflammation may provide a way to substantially delay the progression of AD (Heppner et al 2015). Therefore, agents that can lower oxidative stress can be useful for the prevention and/or treatment of Alzheimer's disease and Parkinson's disease, and agents that can diminish spatial memory deficit and/or lower brain levels of pro-inflammatory agents such as TNF-alpha or IL-6 provide drugs for Alzheimer's disease.

The health problems arising from spatial memory deficit, oxidative stress, inflammation, anxiety and sleep disorders, which can impinge on the brain and are common among old people, require preventive and/or therapeutic agents that are relatively free of adverse side effects so that they can be administered on a chronic basis, and capable of crossing the blood-brain barrier so that they can be effective on all organs in the body including the brain. In this regard, a large number of Chinese medicinal herbs have been employed for medicinal purposes over centuries and are known to be suitable for chronic use. Previously, a search for an anxiolytic herbal decoction has led to the development of the Erhuhuanteng, or "BYPA", decoction (Xue and Wong 2008) containing the four Chinese medicinal herbs Radix *Bupleurum chinense* DC ("B"), Rhizoma *Corydalis yanhusuo* WT Wang ("Y"), Caulis *Polygonum multiflorum* Thunb ("P") and Flos *Albizia julibrissin* Durazz ("A"), which has been subjected to acute and chronic toxicity testing and approved for marketing as the anxiolytic Calmlin™ decoction by the Department of Health of Hong Kong SAR. As an anxiolytic decoction, it also may be expected to contain ingredients that can cross the blood-brain barrier. Some general uses (Xie and Huang 1991) and known findings of these four medicinal herbs include:

Radix *Bupleurum chinense* DC is employed as an antipyretic for intermittent fever, for relief of pains in the sides and chest, and to enhance the vitality of the spleen. It also reduces total cholesterol and triglycerides, increases the levels of low-density lipoprotein cholesterol in blood (Shao et al, 2002) and exhibits affinity for a range of receptors including dopamine $D_1$ and $D_2$, muscarinic acetylcholine $M_1$, 5-$HT_1$ and 5-$HT_2$, and $GABA_A$ receptors (Liao et al., 1995).

Rhizoma *Corydalis yanhusuo* WT Wang, has been employed frequently for treatment of all kinds of pain in the chest and abdomen, elevating the threshold of pain and relieving spastic pain. It is also used with other herbs such as *Angelicae dahuricae* for relief of pain (Yuan et al., 2004). It contains dl-tetrahydropalmatine which induces anxiolytic effects in mice when administered orally (Leung et al., 2003). The l-tetrahydropalmatine isomer is a dopamine receptor antagonist (Xu et al, 1989; Mantsch et al, 2007), attenuates oxycodone-induced conditioned place preference (Liu et al 2009) and heroine self-administration (Yue et al 2012), and is approved in China as an analgesic in the form of 'Rotundine' tablets and injection (Chinese Pharmacopoeia Committee (2015).

Caulis*Polygonum multiflorum* Thunb is employed as a sedative for neurasthenia, insomnia and dreamfulness, and to activate blood circulation in collaterals for treatment of aching limbs. It can induce synergistic hypnotic effects when co-administered with pentobarbital (Wing, 2001).

Flos *Albizia julibrissin* Durazz is employed as sedative and tranquilizer for the treatment of fidgetiness and insomnia. It is known to increase pentobarbital-induced sleeping time in a dose dependent manner (Ji et al., 2007; Kang et al., 2000), and exhibit anti-depressant-like effect in the forced swim test (Li et al., 2006).

SUMMARY OF THE INVENTION

A composition is provided which comprises an extract or a dried powder of an extract, the extract being derived from a mixture of plants, the plants comprising either:
(a) Radix *Bupleurum chinense* DC, Rhizoma *Corydalis yanhusuo* WT Wang, and Caulis *Polygonum multiflorum* Thunb, the composition being free of Flos *Albizia julibrissin* Durazz ("BYP");
(b) Radix *Bupleurum chinense* DC, Rhizoma *Corydalis yanhusuo* WT Wang, and Flos *Albizia julibrissin* Durazz, the composition being free of Caulis*Polygonum multiflorum* Thunb ("BYA");
(c) Radix *Bupleurum chinense* DC, Caulis *Polygonum multiflorum* Thunb, and Flos *Albizia julibrissin* Durazz, the composition being free of Rhizoma *Corydalis yanhusuo* WT Wang ("BPA");
(d) Rhizoma *Corydalis yanhusuo* WT Wang, Caulis *Polygonum multiflorum* Thunb, and Flos *Albizia julibrissin* Durazz, the composition being free of Radix *Bupleurum chinense* DC ("YPA");
(e) Radix *Bupleurum chinense* DC and Rhizoma *Corydalis yanhusuo* WT Wang, the composition being free of Caulis*Polygonum multiflorum* Thunb and Flos *Albizia julibrissin* Durazz ("BY");
(f) Radix *Bupleurum chinense* DC and Caulis*Polygonum multiflorum* Thunb, the composition being free of Rhizoma *Corydalis yanhusuo* WT Wang and Flos *Albizia julibrissin* Durazz ("BP");
(g) Radix *Bupleurum chinense* DC and Flos *Albizia julibrissin* Durazz, the composition being free of Rhizoma *Corydalis yanhusuo* WT Wang, and Caulis*Polygonum multiflorum* Thunb ("BA");
(h) Rhizoma *Corydalis yanhusuo* WT Wang and Caulis*Polygonum multiflorum* Thunb, the composition being free of Radix *Bupleurum chinense* DC and Flos *Albizia julibrissin* Durazz ("YP"); or
(i) Caulis*Polygonum multiflorum* Thunb and Flos *Albizia julibrissin* Durazz, the composition being free of Radix *Bupleurum chinense* DC and Rhizoma *Corydalis yanhusuo* WT Wang ("PA").

A pharmaceutical formulation comprising such composition and an excipient is also provided.

A herbal supplement comprising such composition and an excipient is also provided.

A method of reducing the effect of aging and/or treating anxiety and/or treating sleep disorders is provided. The method comprises administering to a subject in need thereof the composition comprising the plants of BYA, or the pharmaceutical formulation or herbal supplement comprising the plants of BYA.

A method of reducing the effect of aging and/or treating anxiety is provided. The method comprises administering to a subject in need thereof the composition comprising the plants of BPA, or the pharmaceutical formulation or herbal supplement comprising the plants of BPA.

A method of reducing the effect of aging is provided. The method comprises administering to a subject in need thereof the composition comprising the plants of BYP, BY, BP, YP, the composition comprising an extract or a dried powder of an extract, the extract being derived from a mixture of plants or comprising a mixture of extracts derived from the plants, the plants comprising Radix *Bupleurum chinense* DC, Rhizoma *Corydalis yanhusuo* WT Wang, Caulis *Polygonum multiflorum* Thunb, and Flos *Albizia julibrissin* Durazz ("BYPA"), or the pharmaceutical formulation or herbal supplement comprising the plants of BYP, BY, BP, YP, or BYPA.

A method of treating anxiety and/or treating sleep disorders is provided. The method comprises administering to a subject in need thereof the composition comprising the plants of YPA or PA, or the pharmaceutical formulation or herbal supplement comprising the plants of YPA or PA.

A method of treating anxiety is provided. The method comprises administering to a subject in need thereof the composition comprising the plants of BA, or the pharmaceutical formulation or herbal supplement comprising the plants of BA.

In addition to the preceding methods addressing individually or jointly the aging, anxiety and sleep-disorder health problems of normal aging subjects, a method of preventing or treating Alzheimer's disease is provided. The method comprises administering to a subject in need thereof the composition comprising the plants of BYP, BYA, BPA, BY, BP, YP or BYPA, or the pharmaceutical formulation or herbal supplement comprising the plants of BYP, BYA, BPA, BY, BP, YP or BYPA.

As well, a method of preventing or treating Parkinson's disease is provided. The method comprises administering to a subject in need thereof the composition comprising the plants BYP, BYA, BPA, BY, BP, YP or BYPA, or the pharmaceutical formulation or herbal supplement comprising the plants of BYP, BYA, BPA, BY, BP, YP or BYPA.

A method of preparing a pharmaceutical formulation or herbal supplement of the composition is also provided. The method comprises the steps of:
(i) heating a first powder of one or more of the plants in the presence of a solvent to form a suspension;
(ii) collecting the supernatant from the suspension;
(iii) heating the residue from the suspension in the presence of a second solvent to form a second suspension;
(iv) collecting the supernatant from the second suspension;
(v) combining the supernatants to form a third suspension;

(vi) filtering the third suspension to form a filtered third suspension;
(vii) heating the filtered third suspension to form a concentrate;
(viii) dehydrating the concentrate to form a dehydrated residue;
(ix) forming a second powder from the dehydrated residue;
(x) drying the second powder to form a powdered extract of the one or more of the plants;
(xi) if the powdered extract of step (x) comprises an extract of the plants from which the composition is derived, combining the powdered extract with an excipient to yield a pharmaceutical formulation or herbal supplement comprising the composition; and
(xii) optionally repeating steps (i)-(iv) and optionally repeating any one or more of steps (v)-(x) for any remaining plants from which the composition is derived, combining each of the second suspensions, the third suspensions, the filtered third suspensions, the concentrates, the dehydrated residues, or the second powders to form a final powdered extract, and mixing the final powdered extract with an excipient to yield a pharmaceutical formulation or herbal supplement comprising the composition.

Other objects and features will be in part apparent and in part pointed out hereinafter.

BRIEF DESCRIPTION OF THE DRAWINGS

FIG. 1A shows the percentage of entries into novel arm, and FIG. 1B shows time spent in the novel arm. * ($p<0.05$),  ($p<0.01$), or * ($p<0.001$) indicates a significant difference between the two groups of mice connected by a line based on the Newman-Keuls test after one-way ANOVA.

FIG. 2A shows TNF-alpha level in the brain; FIG. 2B shows IL-6 level in the brain; and FIG. 2C shows the level of the lipid peroxidation indicator malondialdehyde (MDA) in the brain. * ($p<0.05$),  ($p<0.01$), or * ($p<0.001$) indicates a significant difference between the two groups of mice connected by a line based on the Newman-Keuls test after one-way ANOVA.

FIG. 5A shows the locomotor activity score in different treatment groups; FIG. 5B shows muscle coordination monitored in terms of length of stay of animals on rotarod; and FIG. 5C shows extents of any cognitive impairment in the form of decreased step-through latency in the step-through passive avoidance test. Mice were administered with vehicle ("Veh", 0.9% NaCl), diazepam ("DZ", 1 or 3 mg/kg), a single-herb or a herbal mixture extract (120 mg/kg) as labeled on the X-axis. Data represent mean±S.E.M. (n>16). *** ($p<0.001$) indicates a significant difference between DZ-treated mice and Veh-treated mice based on the Newman-Keuls test after one-way ANOVA. There was no significant difference between any group of single-herb or herbal mixture extract-treated mice and the Veh-treated mice based on the Newman-Keuls test after one-way ANOVA in FIG. 5A, 5B or 5C.

DESCRIPTION OF THE PREFERRED EMBODIMENTS

Figure 1A:
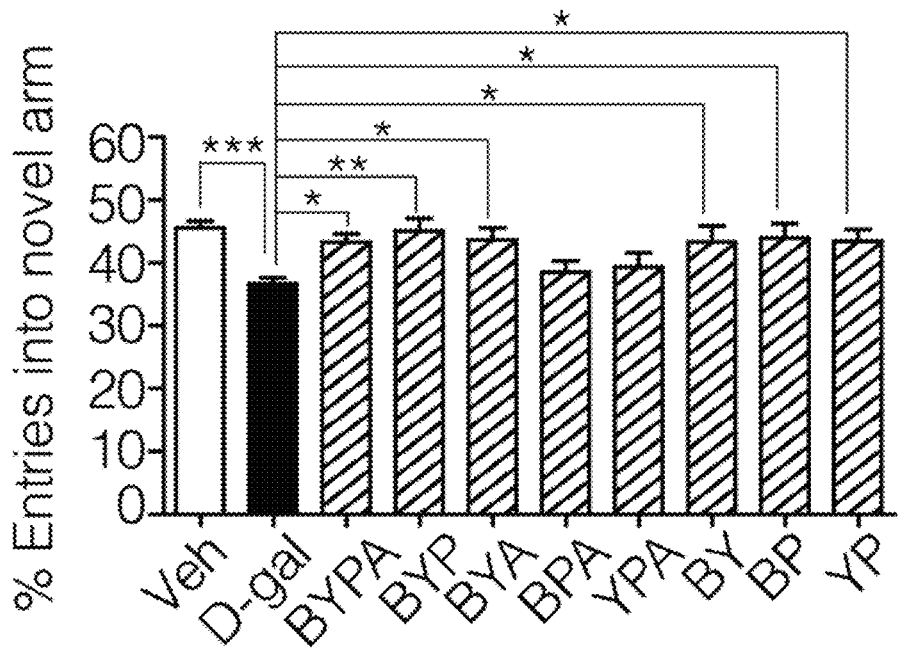
FIGS. 1A and 1B are bar graphs showing the anti-aging effects of herbal extracts regarding spatial memory. The "D-gal" label on the X-axis represents D-galactose-treated control mice administered daily with 150 mg/kg D-galactose by subcutaneous injection for 8 weeks together with daily oral administration of only vehicle (0.9% NaCl), and the "BYPA", "BYP", "BYA", "BPA", "YPA", "BY", "BP" or "YP" label on the X-axis represents mice administered daily with 150 mg/kg D-galactose by subcutaneous injection for 8 weeks together with daily oral administration of the labeled herbal extract (120 mg/kg) prior to the Y-maze test. The "Veh" label on the X-axis represents mice which received daily injection of the vehicle as well as daily oral feeding of the vehicle for 8 weeks prior to a Y-maze test, and no D-galactose or herbal extract. Data represent mean±S.E.M. (n≥12).

It has been discovered that a number of extracts made from the two-herb, three-herb and four-herb mixtures comprising Radix *Bupleuri chinense* DC (B), Rhizoma *Corydalis yanhusuo* W. T. Wang (Y), Caulis *Polygoni mulnflorum* Thunb (P) and Flos *Albiziae julibrissin* Durazz (A) are effective in preventing or treating the age-related health problems of memory deficit, increased oxidative stress, neuroinflammation, anxiety and sleep-disorder. Such mixtures exhibit significant anti-aging effects in a murine model in terms of alleviation of D-galactose-induced accelerated aging observable as spatial memory deficit measured with Y-maze test, neuroinflammation indicated by elevated brain levels of TNF-alpha and IL-6, or enhanced oxidative stress indicated by elevated brain levels of MDA. On account of the overlapping phenotypic symptoms of aging and age-related degenerative diseases, the anti-aging effects observed with respect to memory deficit, neuroinflammation and oxidative stress are applicable to the prevention and treatment of Alzheimer's disease, and the anti-aging effect with respect to oxidative stress is applicable to the prevention and treatment of Parkinson's disease. In addition, some of the herbal decoctions based on the B, Y, P and A herbs displayed anxiolytic effects that can be employed to treat anxiety disorders, and/or sedative effects that can be employed to treat sleep disorders. None of the useful herbal decoctions of BYP, BYA, BPA, YPA, BY, BP, BA, YP, PA and BYPA gave rise to any significant adverse side effects at the maximum oral dosage tested in the form of increased or decreased locomotor activity, reduced muscle coordination on the rotarod, or anterograde amnesia in the step-through passive avoidance test in murine models.

The composition comprises an extract or a dried powder of an extract. The extract can be derived from a mixture of plants as described herein. Alternatively, the extract can comprise a mixture of extracts derived from the plants as described herein.

The composition can comprise a decoction of the extract or a dried powder of the decoction.

A composition is provided which comprises the extract derived from the plants, the plants comprising Radix *Bupleurum chinense* DC, Rhizoma *Corydalis yanhusuo* WT Wang, and Caulis Polygonum multiflorum Thunb ("BYP"). The composition is free of Flos *Albizia julibrissin* Durazz. The mixture of plant extracts can be derived from a powder blend comprising B, Y and P having a weight ratio of about [0.5-2.0]:[0.5-2.0]:[0.5-2.0], and preferably about 1.4:1:1.

A composition is provided which comprises the extract derived from the plants, the plants comprising Radix *Bupleurum chinense* DC, Rhizoma *Corydalis yanhusuo* WT Wang, and Flos Albizia julibrissin Durazz ("BYA"). The composition is free of Caulis*Polygonum multiflorum* Thunb. The extract can be derived from a powder blend comprising B, Y and A having a weight ratio of about [0.5-2.0]:[0.5-2.0]:[0.1-1.5], and preferably about 1.4:1:1.

A composition is provided which comprises the extract derived from the plants, the plants comprising Radix *Bupleurum chinense* DC, Caulis *Polygonum multiflorum* Thunb, and Flos *Albizia julibrissin* Durazz ("BPA"). The composition is free of Rhizoma *Corydalis yanhusuo* WT Wang. The extract can be derived from a powder blend comprising B, P and A having a weight ratio of about [0.5-2.0]:[0.5-2.0]:[0.1-1.5], and preferably about 1.4:1:1.

A composition is provided which comprises the extract derived from the plants, the plants comprising Rhizoma *Corydalis yanhusuo* WT Wang, Caulis *Polygonum multiflorum* Thunb, and Flos *Albizia julibrissin* Durazz ("YPA"). The composition is free of Radix *Bupleurum chinense* DC. The extract can be derived from a powder blend comprising Y, P and A having a weight ratio of about [0.5-2.0]:[0.5-2.0]:[0.1-1.5], and preferably about 1:1:1.

A composition is provided which comprises the extract derived from the plants, the plants comprising Radix *Bupleurum chinense* DC and Rhizoma *Corydalis yanhusuo* WT Wang ("BY"). The composition is free of Caulis*Polygonum multiflorum* Thunb and Flos *Albizia julibrissin* Durazz. The extract can be derived from a powder blend comprising B and Y having a weight ratio of about [0.5-2.0]:[0.5-2.0], and preferably about 1.4:1

A composition is provided which comprises the extract derived from the plants, the plants comprising Radix *Bupleurum chinense* DC and Caulis*Polygonum multiflorum* Thunb ("BP"). The composition is free of Rhizoma *Corydalis yanhusuo* WT Wang and Flos *Albizia julibrissin* Durazz. The extract can be derived from a powder blend comprising B and P having a weight ratio of about [0.5-2.0]:[0.5-2.0], and preferably about 1.4:1.

A composition is provided which comprises the extract derived from the plants, the plants comprising Radix *Bupleurum chinense* DC and Flos *Albizia julibrissin* Durazz ("BA"). The composition is free of Rhizoma *Corydalis yanhusuo* WT Wang, and Caulis *Polygonum multiflorum* Thunb. The extract can be derived from a powder blend of B and A having a weight ratio of about [0.5-2.0]:[0.1-1.5], and preferably about 1.4:1.

A composition is provided which comprises the extract derived from the plants, the plants comprising Rhizoma *Corydalis yanhusuo* WT Wang, and Caulis*Polygonum multiflorum* Thunb ("YP"). The composition is free of Radix *Bupleurum chinense* DC and Flos *Albizia julibrissin* Durazz. The extract can be derived from a powder blend comprising Y and P having a weight ratio of about [0.5-2.0]:[0.5-2.0], and preferably about 1:1.

A composition is provided which comprises the extract derived from the plants, the plants comprising Caulis *Polygonum multillorum* Thunb and Flos *Albizia julibrissin* Durazz ("PA"). The composition is free of Radix *Bupleurum chinense* DC and Rhizoma *Corydalis yanhusuo* WT Wang. The extract can be derived from a powder blend comprising P and A having a weight ratio of about [0.5-2.0]:[0.1-1.5], and preferably about 1:1.

A composition is provided which comprises the extract derived from the plants, the plants comprising Radix *Bupleurum chinense* DC, Rhizoma *Corydalis yanhusuo* WT Wang, Caulis *Polygonum multiflorum* Thunb and Flos *Albizia julibrissin* Durazz ("BYPA"). The extract can be derived from a powder blend comprising B, Y, P and A having a weight ratio of about [0.5-2.0]:[0.5-2.0]:[0.5-2.0]:[0.1-1.5], and preferably about 1.4:1:1:1.

The mixtures of plants in the compositions as described above can be derived from a powder blend of 0 to about 95 wt. % of Radix *Bupleurum chinense* DC, 0 to about 95 wt. % *Corydalis yanhusuo* WT Wang, 0 to about 95 wt. % Caulis *Polygonum multillorum* Thunb, and 0 to about 75 wt. % Flos *Albizia julibrissin* Durazz, based on the total weight of these dried plants in the mixture. Preferably, the mixtures of plants in the compositions as described above are derived from a powder blend of 0 to about 95 wt. % of Radix *Bupleurum chinense* DC, 0 to about 95 wt. % *Corydalis yanhusuo* WT Wang, 0 to about 95 wt. % Caulis*Polygonum multiflorum* Thunb, and 0 to about 75 wt. % Flos *Albizia julibrissin* Durazz based on the total weight of these plants in the mixture. More preferably, the mixtures of plants in the compositions as described above are derived from a powder blend of 32 wt. % to about 58 wt. % of Radix *Bupleurum chinense* DC where it is a constituent, 23 wt. % to about 50 wt. % *Corydalis yanhusuo* WT Wang where it is a constituent, 23 wt. % to about 50 wt. % Caulis *Polygonum multiflorum* Thunb where it is a constituent, or 23 wt. % to about 50 wt. % Flos *Albizia julibrissin* Durazz where it is a constituent, based on the total weight of these dried plants in the mixture.

A pharmaceutical formulation can be prepared. The pharmaceutical formulation comprises any of the above compositions and an excipient. The excipient can be any available excipient used in the pharmaceutical arts.

A herbal supplement can be prepared. The herbal supplement comprises any of the above compositions and an excipient. The excipient can be any available excipient used in the herbal supplement or pharmaceutical arts.

A method of reducing the effect of aging and/or treating anxiety and/or treating sleep disorders is provided. The method comprises administering to a subject in need thereof the composition as described herein comprising the extract from the plants BYA, or the pharmaceutical formulation or herbal supplement as described herein comprising the extract from the plants BYA.

A method for reducing the effect of aging and/or treating anxiety is provided. The method comprises administering to a subject in need thereof the composition as described herein comprising the extract from the plants BPA, or the pharmaceutical formulation or herbal supplement as described herein comprising the extract from the plants BPA.

A method of reducing the effect of aging is provided. The method comprises administering to a subject in need thereof the composition as described herein comprising the extract from the plants BYP, BY, BP, YP or BYPA, or the pharmaceutical formulation or herbal supplement as described herein comprising the extract from the plants BYP, BY, BP, YP or BYPA.

As described in Example 2, spatial memory deficit, neuroinflammation and oxidative stress are three manifestations of normal aging as well as accelerated aging induced by D-galactose. On this basis, agents that can ameliorate any of these three types of physiological and biochemical changes in an animal model can be regarded as useful drugs for treating the symptoms of the aging process. Accordingly, a herbal composition comprising mixture BYP, BYA, BPA, BY, BP, YP or BYPA, or the herbal supplement comprising mixture BYP, BYA, BPA, BY, BP, YP or BYPA represents, on account of its demonstrated ability to increase percentile novel arm entries or percentile time spent in the Y-maze, or reduce the brain level of TNF-alpha, IL-6 or MDA significantly, a drug for treating the effects of normal aging. Since the neural protective effects of BYP, BYA, BPA, BY, BP, YP or BYPA extract were each obtained through daily oral administration, their active ingredients were stable in the gastrointestinal tract to induce the anti-aging effects.

A method of treating anxiety and/or treating sleep disorders is provided. The method comprises administering to a subject in need thereof the composition as described herein comprising the extract from the plants YPA or PA, or the pharmaceutical formulation or herbal supplement as described herein comprising the extract from the plants YPA or PA.

A method of treating anxiety is provided. The method comprises administering to a subject in need thereof the composition as described herein comprising the extract from the plants BA, or the pharmaceutical formulation or herbal supplement as described herein comprising the extract from the plants BA.

As described in Example 3, the two-herb extracts BA and PA, and the three-herb extracts BYA, BPA and YPA induced significant anxiolytic effects at varying dosages as evidenced by increases in percentage time spent by the mice in the open arms in the elevated plus-maze test, indicating that these five herbal decoctions can be employed to treat anxiety disorders. Significant sedation was induced by the two-herb extract PA, and the three-herb extracts BYA and YPA, indicating that these three herbal decoctions can be employed to treat sleep disorders.

Figure 4:
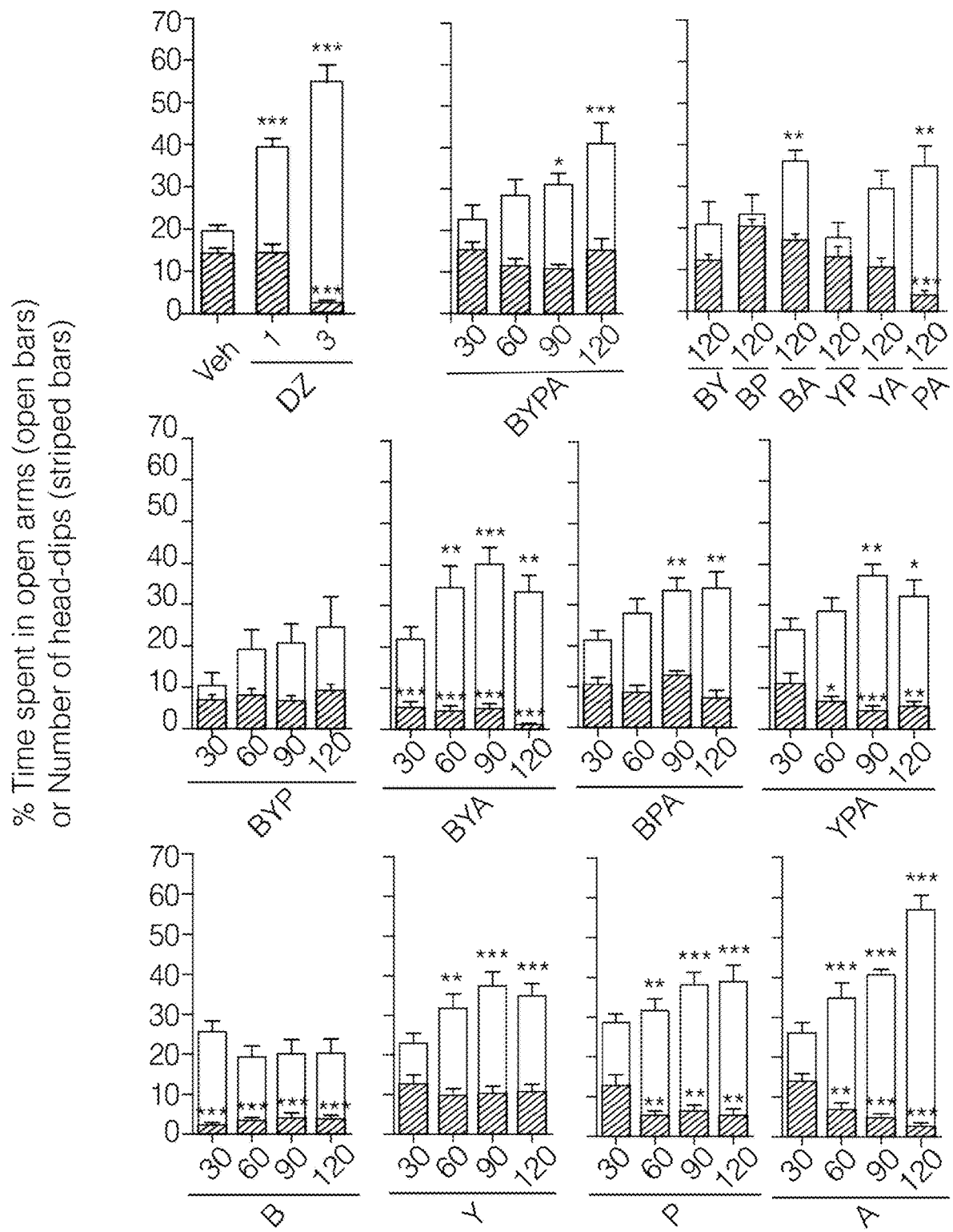
FIG. 4 are bar graphs showing anxiolytic and sedative effects of herbal extracts. Mice were orally administered with vehicle without any drug or herbal extract ("Veh", 0.9% NaCl), or diazepam ("DZ", 1 or 3 mg/kg), or a herbal extract (30, 60, 90 or 120 mg/kg) as labeled on the X-axis of each panel 35 minutes prior to an elevated plus-maze test followed by a holeboard test. The Y-axis represents mean±S.E.M. (n>18) of the percentage of time spent in open arms in the elevated plus-maze test (open bars) or the number of head dips in the holeboard test (striped bars). Significant differences of DZ-treated or herbal extract-treated mice from Veh-treated mice based on the Newman-Keuls test after one-way ANOVA are indicated by * ($p<0.05$),  ($p<0.01$), or * ($p<0.001$). The numbers 1, 3, 30, 60, 90 or 120 on the X-axis of each panel indicate the dosage administered in mg/kg.

With respect to anxiolytic and sedative effects, the results in FIG. 4 revealed unexpected antagonisms and synergisms among the B, Y, P and A herbs. For example, although the single herbs Y, P and A all induced anxiolysis at 60-120 mg/kg, the BYP, BY, BP, YP and YA extracts were devoid of anxiolytic effect even at 120 mg/kg. The lack of anxiolysis by YP and YA, where both constituent herbs in the decoction were anxiolytic, was especially notable. As well, although each of the B, P and A herbs when administered by itself at 30 mg/kg or 60/mg upwards gave rise to significant sedation in mice, none of the BYP, BPA, BY, BP, BA, YP, YA, and BYPA extracts induced significant sedation at 120 mg/kg. These findings clearly demonstrate that the medicinal properties of the BYP, BPA, BY, BP, BA, YP, YA, and BYPA combinations derived from the B, Y, P and A herbs differ distinctively from the sum of the medicinal properties displayed by their constituent herbs with respect to the ability to induce sedation. Such antagonisms and synergisms between medicinal herbs can be utilized to enhance therapeutic efficacy and eliminate undesirable side effects.

A method of preventing or treating Alzheimer's disease is provided. The method comprises administering to a subject in need thereof the composition as described herein comprising the extract from the plants BYP, BYA, BPA, BY, BP, YP or BYPA, or the pharmaceutical formulation or herbal supplement as described herein comprising the extract from the plants BYP, BYA, BPA, BY, BP, YP or BYPA.

As described in Example 2, spatial memory deficit, neuroinflammation and oxidative stress are manifestations of Alzheimer's disease as well, and an herbal composition comprising mixture BYP, BYA, BPA, BY, BP, YP or BYPA, or the herbal supplement comprising mixture BYP, BYA, BPA, BY, BP, YP or BYPA also represents, on account of its demonstrated ability to increase percentile novel arm entries or percentile time spent in the Y-maze, or reduce the brain level of TNF-alpha, IL-6 or MDA significantly, a drug for the prevention and/or treatment of Alzheimer's disease. Among the different herbal extracts tested, it is notable that the BYP and BY extracts displayed anti-aging and anti-Alzheimer's disease effects with respect to all five experimental parameters tested in the D-galactos treated mice: they significantly increased both entries into and time spent in the novel arm in the Y-maze, and reduced the brain levels of TNF-alpha, and IL-6 as well as MDA. The BP, YP and BYPA extracts also scored positively with respect to four out of five of the parameters.

As well, a method of preventing or treating Parkinson's disease is provided. The method comprises administering to a subject in need thereof the composition as described herein comprising the extract from the plants BYP, BYA, BPA, BY, BP, YP or BYPA, or the pharmaceutical formulation or herbal supplement as described herein comprising the extract from the plants BYP, BYA, BPA, BY, BP, YP or BYPA.

Since oxidative stress is a manifestation of Parkinson's disease, a herbal composition comprising mixture BYP, BYA, BPA, BY, BP, YP or BYPA, or the herbal supplement comprising mixture BYP, BYA, BPA, BY, BP, YP or BYPA also represents, on account of its demonstrated capacity to reduce the brain level of MDA in D-galactose treated mice significantly as described in Example 2, a drug for the prevention and/or treatment of Parkinson's disease.

As described in Example 4, none of the one-, two-, three- or four-herb extracts prepared from B, Y , P and A induced any significant alteration in locomotor activity, deficit in muscle coordination or anterograde amnesia at 120 mg/kg. Therefore the BYP, BYA, BPA, YPA, BY, BP, BA, YP, PA and BYPA compositions as described herein, which were found to provide protection against normal aging, prevention or treatment of Alzheimer's disease, prevention or treatment of Parkinson's disease, treatment of anxiety and/or treatment of sleep disorders were devoid of the undesirable side effects of altered locomotor activity, muscle incoordination or anterograde amnesia. Furthermore, among these ten compositions, the BYP, BPA, BY, BP, YP and BYPA compositions displayed anti-aging effects, but no significant sedative effect on account of evident antagonistic interactions between their constituent herbs even though single B, P and A herbs gave rise to significant sedation when administered alone. The lack of sedative effects beneficially facilitates the usage of these six compositions on a chronic basis as anti-aging, anti-Alzheimer's disease and/or anti-Parkinson's disease agents.

Subjects being treated with the methods of the invention are typically human but may be mammals if in need of anti-aging or anxiolytic treatment. The composition or herbal supplement can be added to an animal feed.

A subject in need of treatment for reducing the effect of aging can be a human subject who is thirty years of age or older, or who is experiencing age-related changes such as decreased spatial memory or mental acuity.

A subject in need of prevention or treatment of Alzheimer's disease can be a subject who is at risk of or diagnosed for Alzheimer's disease based on cognitive and family histories, mental status, neurological examination and neuroimaging (Mendez, 2006; Schroeter et al 2009).

A subject in need of prevention or treatment of Parkinson's disease can be a subject who is at risk of or diagnosed for Parkinson's disease based on its primary symptoms of tremor, rigidity, bradykinesia and postural instability (NIH-SeniorHealth 2012). The subject may present a wide range of other secondary symptoms.

The term "treating" as used herein includes achieving a therapeutic benefit. By therapeutic benefit is meant prevention, amelioration, or eradication of the underlying disorder being treated. For example, in an anxiolytic subject, therapeutic benefit includes prevention, amelioration or eradication of the underlying anxiety. Also, a therapeutic benefit is achieved with the eradication, amelioration, or prevention of one or more of the physiological symptoms associated with the underlying disorder such that an improvement is observed in the subject, notwithstanding that the subject may still be afflicted with the underlying disorder. For example, administration of the pharmaceutical formulation or herbal supplement to a subject experiencing anxiety provides therapeutic benefit not only when the subject experiences lesser anxiety, but also when an improvement is observed in the subject with respect to other disorders that accompany anxiety, like heart palpitations, shortness of breath, nausea, dizziness, muscle tension, dry mouth and the like.

The compositions can be administered as a pharmaceutical formulation or herbal supplement containing an effective amount, i.e., in an amount effective to achieve therapeutic or prophylactic benefit from the extract derived from the mixture of plants or comprising a mixture of extracts derived from the plants and a pharmaceutically acceptable carrier. The actual amount effective for a particular application will depend on the subject (e.g., age, weight, etc.), the condition being treated, and the route of administration. Determination of an effective amount is well within the capabilities of those skilled in the art, especially in light of the disclosure herein. The effective amount for use in humans can be determined from animal models (Reagan-Shaw et al, 2016) based on the body surface area (BSA) normalization method suggested by the Food and Drug Administration (Center for Drug Evaluation and Research, 2002).

The pharmaceutical formulations and herbal supplements described herein can be delivered to the subject using a wide variety of routes or modes of administration, such as oral, skin lotion, skin cream, skin patch and parenteral (e.g., intravenous or subcutaneous injection). The most preferred routes for administration are oral, skin lotion, skin cream and skin patch.

The pharmaceutical formulations and herbal supplements may be prepared in conventional manner using one or more pharmaceutically acceptable excipients comprising carriers, diluents, and auxiliaries which facilitate processing of the active compounds into preparations that can be used physiologically (see, e.g., Remington's Pharmaceutical Sciences). The selected formulation is dependent upon the route of administration chosen.

For oral administration, formulations of the compositions can be prepared readily by combining the composition with pharmaceutically acceptable excipients well known in the art. Such excipients enable the compositions to be formulated as tablets, pills, dragees, capsules, liquids, gels, syrups, slurries, suspensions, wafers, and the like, for oral ingestion by a subject to be treated. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

The active ingredient (i.e., the extract from the mixture of plants) constitutes about 20, 30, 40, 50, 60, 70, 80 or 90% by weight of the oral dosage form, the remainder comprising suitable excipient(s).

The compositions described herein can be made by the following process. A powder blend comprising a powder of each plant in the mixture is boiled in a solvent (e.g., 2 L of 5% acetic acid) for about two hours to form a suspension. The supernatant from the suspension is collected. The residue separated from the suspension is boiled in a solvent (e.g., 2 L of 5% acetic acid) to form a second suspension. The supernatant from the second suspension is collected, and the supernatants are combined to form a third suspension. The third suspension is filtered and then boiled down in volume (e.g., to about 100 ml) to form a concentrate. The concentrate is dehydrated in an oven (e.g., at about 92° C.) to form a dehydrated residue. The dehydrated residue is mixed with a solvent (e.g., 100% ethanol), finely powdered, and re-dried (e.g., at about 92° C.) to form the powdered plant extracts. Because a decoction of Chinese medicine derived from more than one plants can be, and is known to be, prepared either through the extraction of a mixture of more than one medicinal plant or through the pooling of individual extracts made from the individual plants in the mixture, the decoction obtained by processing a powder blend comprising a powdered mixture of herbal plants through steps (i) to (x) as described above can also be obtained instead by processing the individual powdered plants belonging to the mixture separately and pooling the individual extracts following step (v), (vi), (vii), (viii), (ix) or (x) to form the desired powdered decoction from the mixture of plants.

The mixture of plants extracted can contain or consist essentially of the mixture of BYP, and the weight ratio of the powder of each plant in the powder blend is about 1.4:1:1 of B:Y:P.

The mixture of plants extracted can contain or consist essentially of the mixture of BYA, and the weight ratio of the powder of each plant in the powder blend is about 1.4:1:1 of B:Y:A.

The mixture of plant extracts can contain or consist essentially of the mixture of BPA, and the weight ratio of the powder of each plant in the powder blend is about 1.4:1:1 of B:P:A.

The mixture of plants extracted can contain or consist essentially of the mixture of YPA, and the weight ratio of the powder of each plant in the powder blend is about 1:1:1 of Y:P:A.

The mixture of plants extracted can contain or consist essentially of the mixture of BY, and the weight ratio of the powder of each plant in the powder blend is about 1.4:1 of B:Y.

The mixture of plants extracted can contain or consist essentially of the mixture of BP, and the weight ratio of the powder of each plant in the powder blend is about 1.4:1 of B:P.

The mixture of plants extracted can contain or consist essentially of the mixture of BA, and the weight ratio of the powder of each plant in the powder blend is about 1.4:1 of B:A.

The mixture of plants extracted can contain or consist essentially of the mixture of YP, and the weight ratio of the powder of each plant in the powder blend is about 1:1 of Y:P.

The mixture of plants extracted can contain or consist essentially of the mixture of PA, and the weight ratio of the powder of each plant in the powder blend is about 1:1 of P:A.

The mixture of plants extracted can contain or consist essentially of the mixture of BYPA, and the weight ratio of the powder of each plant in the powder blend is about 1.4:1:1:1 of B:Y:P:A.

Having described the invention in detail, it will be apparent that modifications and variations are possible without departing from the scope of the invention defined in the appended claims.

EXAMPLES

The following non-limiting examples are provided to further illustrate the present invention.

Example 1

Preparation of Extracts of Herbal Mixtures and Animal Test Preparation

Preparation of Extracts of Herbal Mixtures. To prepare the decoction with the four-herb BYPA formula, 65 g B, 45 g Y, 45 g P and 45 g A were powdered and boiled in 2 L of 5% acetic acid for 2 hours. The supernatant was collected and the residue was re-boiled in 2 L of 5% acetic acid for 2 hours. The two batches of supernatant were pooled together, filtered and boiled down to a volume of 100 ml prior to dehydration in an oven at 92° C. Thereupon 300 ml 100% ethanol was added to the dehydrated residue, which was finely powdered and re-dried at 92° C. The dried extract was weighed and powdered.

To prepare the extract from a subset of the four-herb BYPA decoction, one or more of the four constituent herbs was omitted in performing the same procedure without changing the amounts of the remaining herbs, e.g. only 65 g B, 45 g Y and 45 g P were boiled in 2 L of 5% acetic acid for 2 hours and so on in preparing the extract of the three-herb BYP-decoction, or only 45 g P and 45 g A were boiled in 2 L of 5% acetic acid for 2 hours and so on in preparing the extract of the two-herb PA-decoction.

Comparative Composition. In certain experiments, Diazepam (DZ) obtained from Sigma (St. Louis, Mo., USA) was used as a comparative anxiolytic. Diazepam was dissolved in 0.9% NaCl in the presence of 1% DMSO for animal tests, and administered to mice in a delivery volume of 10 ml/kg through the oral route.

Animal Preparation. Male ICR mice were housed in groups of five to ten with food and water ad libitum and kept on a 08:00 hour to 20:00 hour light cycle. All animal experiments were conducted in accordance with the Code of Practice for Care and Use of Animals for Experimental Purposes which was approved by the Animal Welfare Advisory Group, the Agriculture, Fisheries and Conservation Department and the Department of Health of Hong Kong SAR. For anti-aging studies, 10 week old mice (30-50 g) were employed. For behavioral studies, 4-6 week old mice (20-35 g) were employed.

Data analysis. Results were expressed as mean±standard error of the mean (S.E.M.). Data were analyzed by the Newman-Keuls test after One-way ANOVA.

Example 2

Anti-Aging Tests

Chronic exposure to D-galactose is a widely studied aging model that causes shortened lifespan in Drosophila and housefly (Jordens et al 1999; Cui et al 2004), and brings about spatial memory deficit, degeneration in the hippocampus and increased oxidative damage in a D-galactose-induced accelerated-aging model of the mouse (Cui et al 2006). In this model, spatial memory impairment was found to be accompanied by a decrease in the density of peripheral-type benzodiazepine receptor (PBR) binding sites on hippocampus synaptosomal membranes (Chen et al 2006). This accelerated-aging model has been employed in the search for medications and/or health supplements to retard the effects of aging in the D-galactose treated animals, revealing that 100 mg/kg i.g. of *Achyranthes bidentata* or *Lycium barbarum* polysaccharide can inhibit nonenzymic glycation (Deng et al 2003), R-α-lipoic acid at 100 mg/kg i.p. can ameliorate cognitive dysfunction and neurodegeneration (Cui 2006), ginsenoside Rg1 at 20 mg/kg i.p. can prevent the cognitive impairment and hippocampus senescence (Zhu et al 2014), and oral asiatic acid at 10 or 20 mg/kg can reduce the elevated levels of brain ROS, TNF-alpha and IL-6 (Chao et al 2015). In the present study, this D-galactose model was applied to 10 week old male ICR mice (n=8-12 per group). The mice were administered daily with 150 mg/kg D-galactose by subcutaneous injection, accompanied by either daily oral administration of the vehicle (0.9% NaCl) in the D-galactose treated control group ("D-gal"), or daily oral administration of one of the BYPA, BYP, BYA, BPA, YPA, BY, BP and YP herbal extracts (120 mg/kg), for an exposure period of 8 weeks. The vehicle group ("Veh") received daily injection of saline (0.9% NaCl) and also oral administration of saline (0.9% NaCl) for 8 weeks. The resultant levels of accelerated aging in the D-gal group, the various herbal extract-treatment groups, and the Veh group were assessed at the end of the 8-week exposure period based on five criteria: (i) body weight; (ii) deficit in spatial memory in the Y-maze test; (iii) levels of the pro-inflammatory cytokine TNF-alpha in the brain; (iv) levels of the pro-inflammatory cytokine IL-6 in the brain; and (v) levels of the oxidative stress marker MDA in the brain. In this regard, there was no significant change in body weight observed after the 8-week exposure period in the Veh group, the D-gal group or any of the herbal treatment groups.

Y-maze test. The test, a two-trial memory task based on a free choice exploration paradigm in a Y-maze, avoids the use of electric shock or deprivation and does not require learning of a rule; and hippocampal damages and chronic stress were shown to cause impaired spatial memory performance in the Y-maze (Dellu et al 2000; Conrad et al 1996). In the study illustrated in FIG. 1, the test was given to each animal at the end of the 8-week exposure to D-galactose using a Y-maze that consisted of three identical arms spaced at an angle of 120° to one another, designated respectively as the 'start arm', 'open arm' and 'novel arm'. At the start of the test, the entrance to the novel arm was closed off, and animal was placed into the start arm and allowed to explore the start arm and the open arm freely for 10 minutes. The animal was removed from the maze for 60 minutes before re-introduced into the maze, now with the entrance to the novel arm also opened up so that the animal could freely explore all three arms for a test period of 5 minutes. During this test period, the number of entries made by the animal into each of the three arms was counted, and the total time spent by the animal in each of the three arms was recorded, where any arm-entry and arm-exit was defined by the placement of all four paws into the arm or outside the arm. Animals with total loss of spatial memory would enter into the three arms randomly, making ~33% of arm entries into the novel arm and spending ~33% of the time in the novel arm. In contrast, animals with either no loss or only partial loss of spatial memory would enter into, and also spend time in, the novel arm preferentially as unexplored territory, causing both of these percentages to exceed 33%.

Figure 1B:
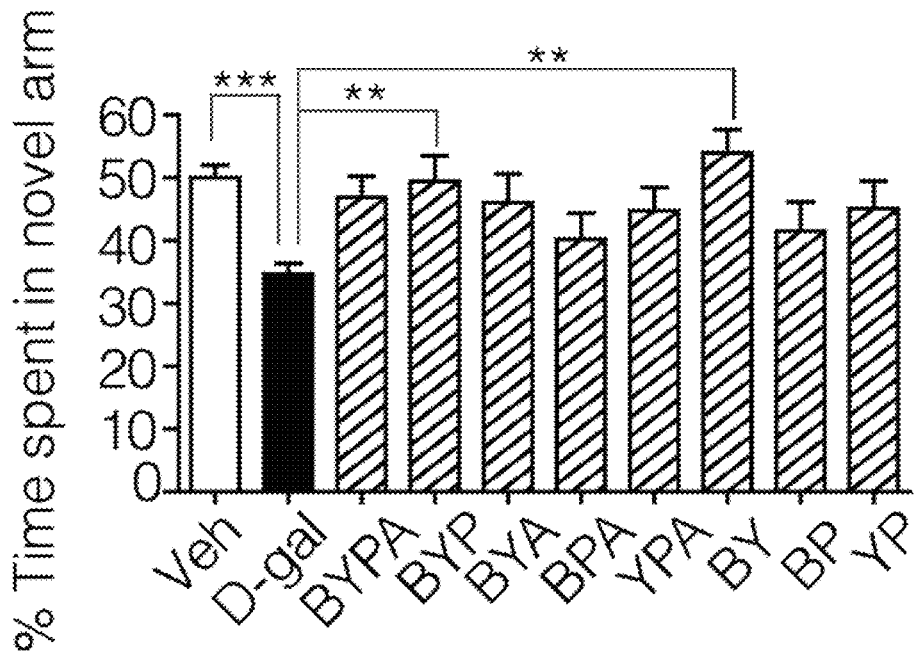

Daily D-galactose injections (150 mg/kg) for 8 weeks induced a significant decrease in entries into, or time spent in, novel arm in the Y-maze with $p<0.001$, indicating a significant loss of spatial memory in the D-gal group compared to the Veh group (FIGS. 1A and 1B). Oral herbal treatment with BYPA, BYA, BY, BP or YP significantly increased the percentile novel arm entries compared to that of the D-gal mice ($p<0.05$); and oral herbal treatment with BYP significantly increased the percentile novel arm entries compared to that of the D-gal mice to $p<0.01$. Oral herbal treatment with BYP or BY also significantly increased the percentile time spent in the novel arm compared to that of the D-gal mice ($p<0.01$).

Neuroinflammation and oxidative stress in brain. Mice were sacrificed by euthanasia at the end of the 8-week exposure period, and the brain was removed and homogenized in phosphate buffer saline, pH 7.2. The levels of TNF-alpha and IL-6 in the brain were measured as neuroinflammation markers using ELISA with solid phase sandwich kits (Invitrogen Corporation, Camerillo, Calif., USA). The minimum detectable levels were 3 pg/ml for each of TNF-alpha and IL-6. TNF-alpha and IL-6 are pro-inflammatory cytokines that were increased in the serum of elderly patients (Franceschi et al, 2007). To assess oxidative stress, the level of the lipid peroxidation product MDA, a widely employed marker for oxidative stress in animal tissues, was estimated using the spectrophotometric assay at 532 nm for reaction between thiobarbituric acid (TBA) and MDA (Pryor, 1989; Ohkawa et al 1979).

Figure 2A:
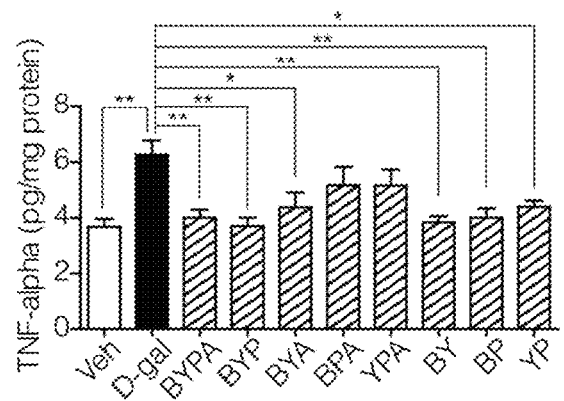
FIGS. 2A, 2B and 2C are bar graphs showing the anti-inflammatory and anti-oxidative effects of herbal extracts on the brains of D-galactose treated mice. Different groups of mice labeled as "Veh", "D-gal", "BYPA", "BYP", "BYA", "BPA", "YPA", "BY", "BP" or "YP" were treated as described in FIG. 1 for 8 weeks before sacrifice and performance of biochemical analysis of brain tissue. Data represent mean±S.E.M. (n=6).
Figure 2B:
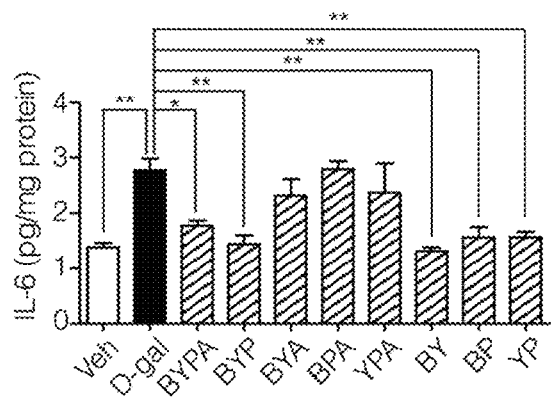

The levels of TNF-alpha and IL-6 were increased in the brains of D-gal mice compared to Veh mice ($p<0.01$). Oral herbal treatment with BYA or YP significantly decreased the brain level of TNF-alpha compared to that of the D-gal mice ($p<0.05$); oral herbal treatment with BYPA, BYP, BY or BP significantly decreased the brain level of TNF-alpha compared to that of the D-gal mice to $p<0.01$ (FIG. 2A). Oral treatment with BYPA significantly decreased the brain level of IL-6 compared to that of the D-gal mice ($p<0.05$); BYP, BY, BP or YP significantly decreased the brain level of IL-6 compared to that of the D-gal mice to $p<0.01$ (FIG. 2B).

Figure 2C:
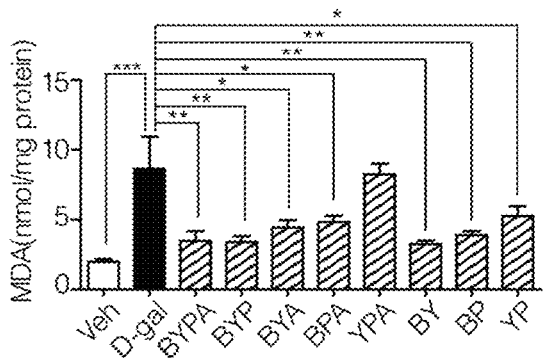

The level of MDA was increased in the brains of D-galactose treated control mice compared to Veh mice ($p<0.001$). Because TNF-alpha is known to induce mitochondrial production of reactive oxygen species (Goossens et al 1995; Baregamian et al 2009), the increase in brain MDA level brought about by exposure to D-galactose could be associated with the neuroinflammation response. In any event, oral herbal treatment with BYA, BPA or YP significantly decreased the brain level of MDA compared to that of the D-gal mice ($p<0.05$); oral herbal treatment with BYPA, BYP, BY or BP significantly decreased the brain level of MDA compared to that of the D-gal mice to $p<0.01$ (FIG. 2C).

Figure 3:
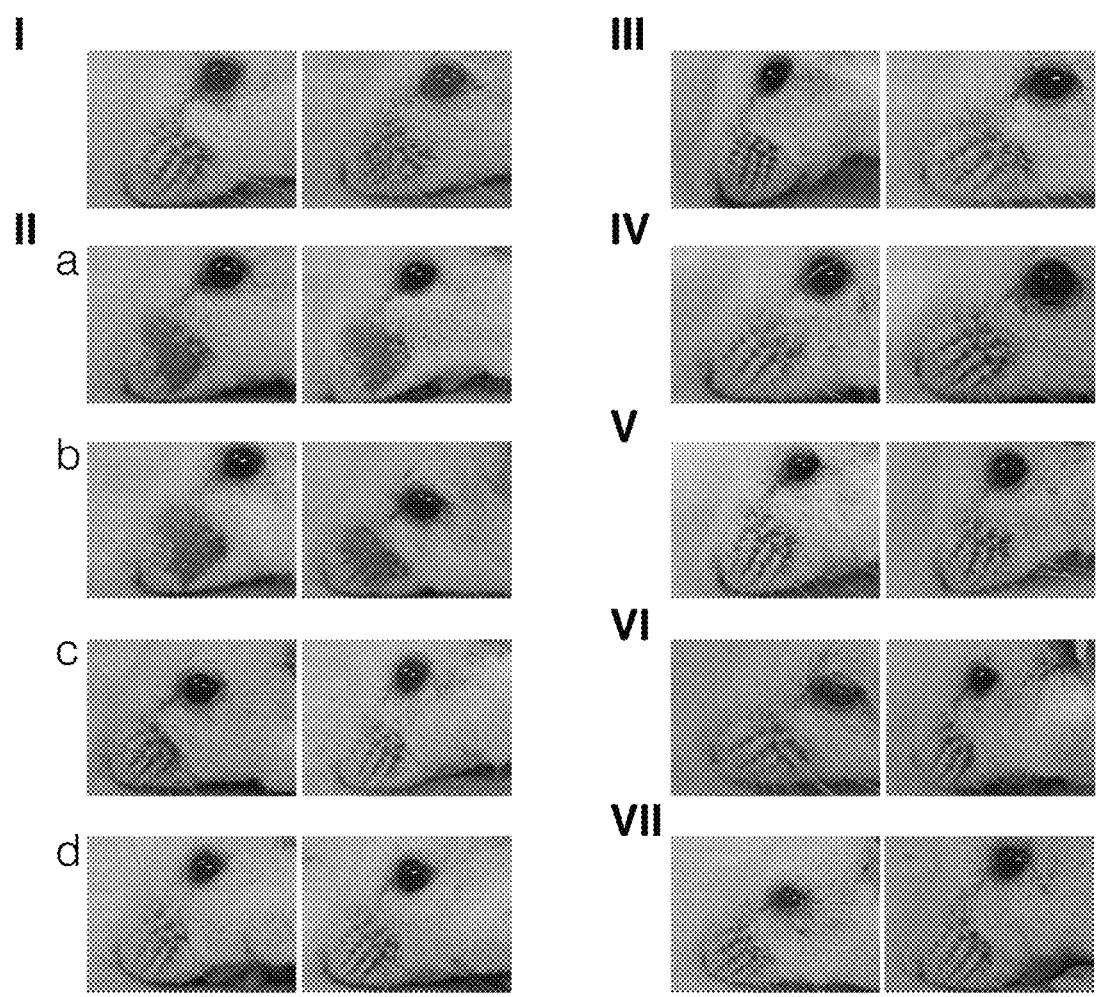
FIG. 3 shows the loss of whiskers induced by D-galactose treatment and prevention by herbal extracts. "Veh", "D-gal", "BYPA", "BYP", "BYA", "BPA" and "YPA" groups of mice were treated for 8 weeks as described in FIG. 1. Photos of whiskers in these groups of mice were taken at the end of the 8-week period. (I) Two normal controls without D-galactose treatment; (IIa, IIb) Four D-galactose treated mice that showed loss of whiskers; (IIc, IId) Four D-galactose treated mice that did not show loss of whiskers; (III) Two of the mice treated with D-galactose and BYPA; (IV) Two of the mice treated with D-galactose and BYP; (V) Two of the mice treated with D-galactose and BYA; (VI) Two of the mice treated with D-galactose and BPA; and (VII) Two of the mice treated with D-galactose and YPA.

Mice treated with D-galactose for 8 weeks showed variable extents of loss of whiskers. Table 1 reports the response of a batch of mice in different treatment groups. The vehicle "Veh" group did not receive any injection of D-galactose, whereas the other groups all received daily injection of D-galactose (150 mg/kg) with or without accompanying daily oral treatment with 120 mg/kg of BYPA, BYP, BYA, BPA or YPA extract. "0" indicates no loss of mystacial macrovibrissae viz. whiskers; and "+" indicates loss of whiskers. Representative mice from the different groups are illustrated in FIG. 3. N=12 mice/group

TABLE 1

|  | Loss of whiskers (% mice) | |
|---|---|---|
| Treatment Group | 0 | + |
| Veh | 100 | 0 |
| D-gal | 50 | 50 |
| D-gal + BYPA | 100 | 0 |
| D-gal + BYP | 100 | 0 |
| D-gal + BYA | 100 | 0 |
| D-gal + BPA | 100 | 0 |
| D-gal + YPA | 100 | 0 |

The results in Table 1 indicated that the BYPA, BYP, BYA, BPA and YPA extracts were capable of conferring protection against the effects of aging in facial tissue.

Spatial memory deficit, neuroinflammation and oxidative stress are three manifestations of normal aging as well as accelerated aging induced by D-galactose. On this basis, agents that can ameliorate any of these three types of physiological and biochemical changes can be regarded as useful drugs for treating the symptoms of the aging process. Accordingly, a herbal composition comprising mixture BYP, BYA, BPA, BY, BP, YP or BYPA, or the herbal supplement comprising mixture BYP, BYA, BPA, BY, BP, YP or BYPA represents, on account of its demonstrated ability to increase percentile novel arm entries (FIG. 1A) or percentile time spent (FIG. 1B) in the Y-maze, or reduce the brain level of TNF-alpha (FIG. 2A), IL-6 (FIG. 2B) or MDA (FIG. 2C) significantly, a drug for treating the effects of normal aging. Since the neural protective effects of BYP, BYA, BPA, BY, BP, YP or BYPA extract in FIGS. 1 and 2 were each obtained through daily oral administration of 120 mg/kg, evidently their active ingredients were stable in the gastrointestinal tract to induce the anti-aging effects.

Since spatial memory deficit, neuroinflammation and oxidative stress are manifestations of Alzheimer's disease as well, a herbal composition comprising mixture BYP, BYA, BPA, BY, BP, YP or BYPA, or the herbal supplement comprising mixture BYP, BYA, BPA, BY, BP, YP or BYPA also represents, on account of its demonstrated ability to increase percentile novel arm entries (FIG. 1A) or percentile time spent (FIG. 1B) in the Y-maze, or reduce the brain level of TNF-alpha (FIG. 2A), IL-6 (FIG. 2B) or MDA (FIG. 2C) significantly, a drug for the prevention and/or treatment of Alzheimer's disease. Among the different herbal extracts tested, it is notable that the BYP and BY extracts displayed anti-aging and anti-Alzheimer's disease effects with respect to all five experimental parameters tested in the D-galactose treated mice: they significantly increased both entries into and time spent in the novel arm in the Y-maze, and reduced the brain levels of TNF-alpha, IL-6 as well as MDA. The BP, YP and BYPA extracts also scored positively with respect to four out of five of the parameters.

Since oxidative stress is a manifestation of Parkinson's disease, a herbal composition comprising mixture BYP, BYA, BPA, BY, BP, YP or BYPA, or the herbal supplement comprising mixture BYP, BYA, BPA, BY, BP, YP or BYPA also represents, on account of its demonstrated capacity to reduce the brain level of MDA in the D-galactose treated mice significantly, a drug for the prevention and/or treatment of Parkinson's disease.

Example 3

Anxiolytic and Sedative Tests

Elevated plus-maze test. Naïve male 4-6 week old mice were randomly separated into groups (n=12-20/group). Vehicle ("Veh", viz. 0.9% NaCl), 30, 60, 90 or 120 mg/kg herbal extract, or 1 or 3 mg/kg DZ was orally administered 35 minutes prior to experiment. The test apparatus consisted of four arms, 25×5 cm each, extending from a central 5×5 cm platform in the shape of a plus sign. Two opposing arms were enclosed by 20 cm opaque high walls, making up the closed arms. The plus maze was elevated 40 cm above ground. Each mouse was placed on to the center of the maze with head facing an open arm. The time periods spent in the open and closed arms were recorded for a period of 5 minutes. An arm entry was recorded when all four paws were inside the arm. At the end of each test, the apparatus was thoroughly cleansed and dried before the start of the next test. An increased percentage of time spent in open arms induced in animals by treatment with a test preparation compared to Veh-treated controls receiving only vehicle is indicative of an anxiolytic-like effect exerted by the test preparation (Kalueff and Tuohimaa, 2004; Treit et al., 1993).

Holeboard test. After the elevated plus-maze test, the test mice were subjected to the holeboard test. The holeboard apparatus was a wooden box, 60×60×20 cm, with four holes of 3 cm diameter evenly spaced on the floor. Each mouse was placed at the center of the holeboard, and the number of head-dips into the holes was recorded for a period of 5 minutes. A head-dip was scored when the head of the mouse was dipped into the hole to the extent that the eyes of the mouse passed below the hole on the floor. After each trial, the floor of the apparatus was thoroughly cleansed and dried before the start of the next test. A decreased number of head-dips induced in animals by treatment with a test substance compared to Veh-treated controls receiving only vehicle is indicative of a sedative effect exerted by the substance (File and Pellow, 1985).

As shown in FIG. 4, single-herb extracts of A, P and Y, starting from a dose of 60 mg/kg, but not single-herb extract of B displayed anxiolytic effects as evidenced by a significant increase in percentage of time spent in open arms in the elevated plus-maze test compared to the Veh-treated mice. Extract P- and extract A-treated mice displayed sedative behavior as evidenced by a decrease in head-dips in the holeboard test starting from 60 mg/kg, whereas extract B-treated mice displayed sedation starting from 30 mg/kg. Extract Y-treated mice did not display any significant sedation evidenced by decrease in head-dips up to 120 mg/kg. With the multiherb extracts, the two-herb extracts BA and PA, and the three-herb extracts BYA, BPA and YPA induced significant anxiolytic effects at varying dosages as evidenced by increases in percentage time spent by the mice in the open arms in the elevated plus-maze test, indicating that these five herbal decoctions can be employed to treat anxiety disorders. Significant sedation was induced by the two-herb extract PA, and the three-herb extracts BYA and YPA, indicating that these three herbal decoctions can be employed to treat sleep disorders. The BYP, BY, BP, YP and YA extracts in contrast did not induce any significant anxiolytic or sedative effect. As reported previously (Xue and Wong 2008), the four-herb BYPA extract induced significant anxiolytic effect but no significant sedation effect.

With respect to anxiolytic and sedative effects, the results in FIG. 4 revealed unexpected antagonisms and synergisms among the B, Y, P and A herbs. For example, although the single herbs Y, P and A all induced anxiolysis at 60-120 mg/kg, the BYP, BY, BP, YP and YA extracts were devoid of anxiolytic effect even at 120 mg/kg. The lack of anxiolysis by YP and YA, where both constituent herbs in the decoction were anxiolytic, was especially notable. As well, although each of the B, P and A herbs when administered by itself at 30 mg/kg or 60/mg upwards gave rise to significant sedation in mice, none of the BYP, BPA, BY, BP, BA, YP, YA, and BYPA extracts induced significant sedation at 120 mg/kg. These findings clearly demonstrate that the medicinal properties of the BYP, BPA, BY, BP, BA, YP, YA, and BYPA combinations derived from the B, Y, P and A herbs differ distinctively from the sum of the medicinal properties displayed by their constituent herbs with respect to the ability to induce sedation. Such antagonisms and synergisms between medicinal herbs can be utilized to enhance therapeutic efficacy and eliminate undesirable side effects (Jiang 2005; Qiu 2007; Wang 2008).

Example 4

Locomotor Activity, Cognition and Muscle Relaxation Tests

Locomotor activity test. Following the elevated plus-maze and holeboard tests, the Veh-treated mice, DZ-treated mice and variously herbal extract-treated mice were assessed for locomotor activity by means of the ZIL-2 apparatus (Beijing Institute of Materia Medica). The test apparatus, with dimensions of 60 cm×60 cm×12 cm, consisted of a transparent plastic cylindrical box equipped with three evenly spaced infrared beams with photodetectors. The number of transitions made across the infrared beams was recorded automatically over a period of 5 minutes. An increase or decrease in the number of transitions indicated a corresponding increase or decrease in the level of locomotor activity (Hui et al, 2002).

Rotarod test. Mice randomly separated into groups (n=15–20/group) were orally administered 35 minutes prior to the rotarod test with vehicle ("Veh", viz. 0.9% NaCl), 1 or 3 mg/kg DZ, or 120 mg/kg of one of the one-, two-, threeor four-herb extracts. The rotarod test for muscle coordination was performed using a custom-built apparatus consisted of a cylinder (2.5 cm diameter) with a textured surface placed 0.5 m above the ground. Prior to oral Veh, DZ or herbal extract administration, the mice were first trained to stay for 2 min on the rotarod revolving at 16 rpm. In the test, the effect of Veh, DZ or herbal extract treatment was examined by placing the mouse on the rotarod and recording the length of time it managed to stay on the rotarod, with cut-off set at 2 min. A significant reduction of the time a group of animals managed to stay on the rotarod compared to Veh-treated controls was indicative of diminished muscle coordination (Karl et al, 2003).

Step-through passive avoidance test. Mice randomly separated into groups (n=15–20/group) were orally administered with vehicle ("Veh", viz. 0.9% NaCl), 1 or 3 mg/kg DZ, or 120 mg/kg of one of the one-, two-, three- or four-herb extracts 35 minutes prior to training trials. The apparatus consisted of a two-chamber box (from Chinese Academy of Chinese Medical Science, Beijing) with one of the chambers being opaque (darkened) and the other transparent (lighted). In the training trials, each mouse was placed into the lighted chamber, and the door connecting the lighted and darkened chambers was opened 10 seconds later. Mice that did not enter the darkened chamber within 15 seconds were excluded from the experiment. In the actual test, after the mouse entered the darkened chamber, the door was closed and a 2-second electric foot shock of 0.4 mA was delivered through the grid floor. Ten seconds later the mouse was transferred from the darkened chamber back to its home cage. After an interval of 24 hours, it was returned to the lighted chamber. The door to the darkened chamber was opened 10 seconds later, and the time taken for the mouse to enter the darkened chamber was recorded as the 'step-through latency', with cut-off set at 300 seconds. A significant decrease in step-through latency observed with any group of animals compared to Veh-treated controls was indicative of impaired working memory in the form of anterograde amnesia (Nazari-Serenj eh et al, 2011).

Figure 5A:
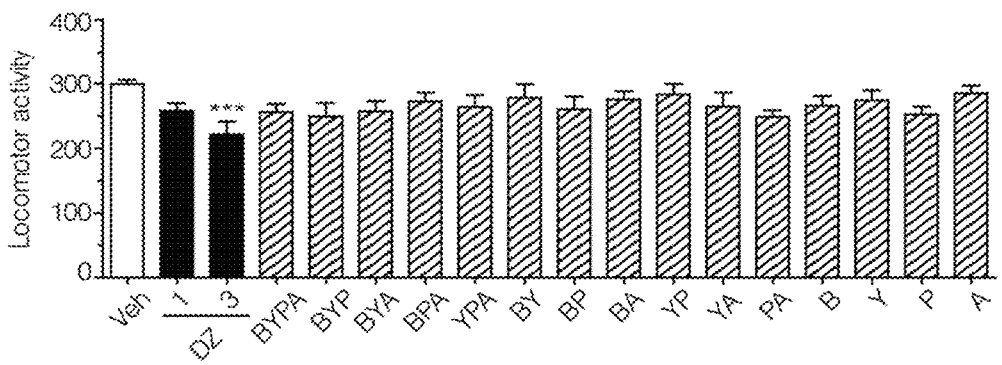
FIGS. 5A, 5B and 5C are bar graphs showing the absence of adverse side effects by herbal extracts.
Figure 5B:
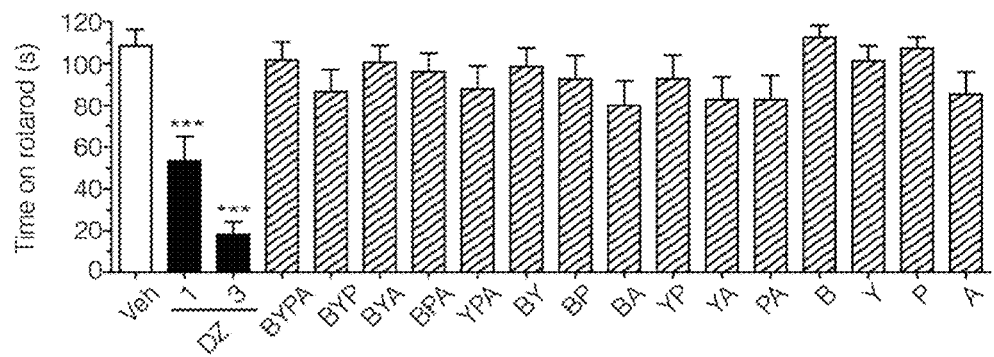
Figure 5C:
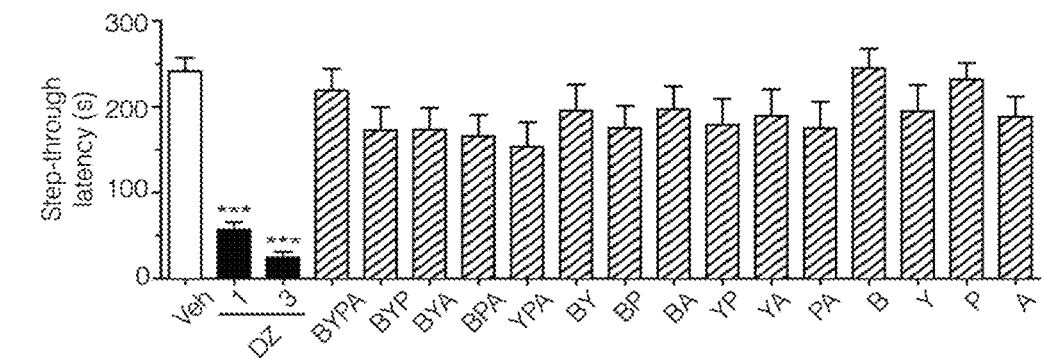

In the locomotor activity test shown in FIG. 5A, there were no significant changes in locomotor activity in mice treated with any of the BYPA, BYP, BYA, BPA, YPA, BY, BP, BA, YP, YA, PA, B, Y, P or A extracts compared to the vehicle-treated mice, whereas 3 mg/kg diazepam induced a significant reduction ($p<0.001$) in locomotor activity. In the rotarod test shown in FIG. 5B, there was also no significant difference between mice treated with any the BYPA, BYP, BYA, BPA, YPA, BY, BP, BA, YP, YA, PA, B, Y, P or A extracts compared to the vehicle-treated mice in the time they managed to stay on the moving rotarod, indicating that there was no significant muscle incoordination in any group of herbal extract-treated mice. In contrast, diazepam at 1 or 3 mg/kg gave rise to a significant reduction in the time of stay on the moving rotarod ($p<0.001$), revealing the induction of muscle incoordination by the drug. In the step-through latency test in FIG. 5C, again there was no significant difference between mice treated with any of the BYPA, BYP, BYA, BPA, YPA, BY, BP, BA, YP, YA, PA, B, Y, P or A extracts compared to the vehicle-treated mice in step-through latency, indicating that no significant anterograde amnesia was induced by any of the herbal extracts tested. In contrast, diazepam at 1 or 3 mg/kg gave rise to significant anterograde amnesia in terms of reduced step-through latency ($p<0.001$).

The results obtained in this Example indicate that none of the one-, two-, three- or four-herb extracts prepared from Radix Bupleuri chinense DC (B), Rhizoma *Corydalis yanhusuo* W.T. Wang (Y), Caulis *Polygoni mulnflorum* Thunb (P) and Flos *Albiziae julibrissin* Durazz (A) induced any significant alteration in locomotor activity, deficit in muscle coordination or anterograde amnesia at 120 mg/kg. Therefore the BYP, BYA, BPA, YPA, BY, BP, BA, YP, PA and BYPA multiherb decoctions, which were found to provide protection against normal aging, prevention or treatment of Alzheimer's disease, prevention or treatment of Parkinson's disease, treatment of anxiety and/or treatment of sleep disorders were devoid of the undesirable side effects of altered locomotor activity, muscle incoordination or anterograde amnesia. Furthermore, among these ten herbal decoctions, the BYP, BPA, BY, BP, YP and BYPA decoctions displayed anti-aging effects, but no significant sedative effect on account of evident antagonistic interactions between their constituent herbs even though single B, P and A herbs gave rise to significant sedation when administered alone (FIG. 4). The lack of sedative effects beneficially facilitates the usage of these six decoctions on a chronic basis as anti-aging, anti-Alzheimer's disease and/or anti-Parkinson's disease agents.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and advantageous results attained.

As various changes could be made in the above compositions and methods without departing from the scope of the invention, it is intended that all matter contained in the above description and shown in the accompanying drawings shall be interpreted as illustrative and not in a limiting sense.

The following references have been cited in the foregoing paragraphs:
1. Alzheimer's Disease Anti-inflammatory Prevention Trial Research Group, 2013. Results of a follow up study to the randomized Alzheimer's disease anti-inflammatory prevention trial (ADAPT). Alzheimer's Dement 9, 714-723.
2. Baregamian N, Song J, Bailey C E et al 2009. Tumor necrosis factor-a and apoposis signal-regulating kinase I control reactive oxygen species release, mitochondrial autophagy and c-Jun N-terminal kinase/p38 phosphorylation during necrotizing eneterocolitis. Oxidative Med Cellular Longevity 2, 297-306.
3. Barja G 2004. Free radicals and aging. Trends Neurosci 27, 595-600.
4. Barnes C A 1988. Aging and the physiology of spatial memory. Neurobiol Aging 9, 563-568.
5. Breitner J C, Baker L D, Montine T J et al, 2011. Extended results of the Alzheimer's disease anti-inflammatory prevention trial. Alzheimers Dement 7, 402-411.
6. Center for Drug Evaluation and Research (2002). Estimating the safe starting dose in clinical trials for therapeutics in adult healthy volunteers, Center for Biologics Evaluation and Research, U.S. Food and Drug Administration: Rockville, Md., USA.
7. Chao P C, Yin M C, Mong M C 2015. Anti-apoptotic and anti-glycative effects of asiatic acid in the brain of D-galactose treated mice. Food Function 6, 542-548.
8. Chen C F, Lang S Y, Zuo P P, Yang N, Wang X Q, Xia C 2006. Effects of D-galactose on the expression of hippocampal peripheral-type benzodiazepine receptor snd spatial memory performance in rats. Psychoneuroendocrinology 31, 805-811.
9. Chinese Pharmacopoeia Committee (2015). Pharmacopoeia of People s Republic of China (Vol. II), 1st edn. China Medical Science & Technology Press: Beijing pp 656-657.
10. Conrad C D, Galea LAM, Kuroda Y, McEwen, B S 1996. Chronic stress impairs rat spatial memory on the Y-maze, and this effect is blocked by tianeptine treatment. Behav Neurosc 110, 1321-34.
11. Cui X, Wang L, Zuo P, Han Z, Fang Z, Li W, Liu J 2004. D-galactose caused life shortening in Drosophila melanogaster and Musca domestica is associated with oxidative stress. Biogerontol 5, 317-326.
12. Cui X, Zuo P, Zhang Q, Li X, Hu Y, Long J, Packer L, Liu J, 2006. Chronic systematic D-galactose exposure induces memory loss, neurodegeneration, and oxidative damage in mice: protective effects of R-alpha-lipoic acid. Journal of Neuroscience Research 84, 647-654.
13. Dellu F et al 2000. Genetic differences in response to novelty and spatial memory using a two-trial recognition task in mice. Neurobiol Learning Memory 73, 31-48.
14. Deng H B, Cui D P, Jiang J M, Feng Y C, Cai N S, Li D D 2003. Inhibiting effects of Achyranthes bidentata or Lycium barbarum polysaccharide on nonenzyme Glycation in D-galactose induced mouse aging model. Biomed Environ Sci 16, 267-275.
15. Fernandez-Checa J C, Fernandez A, Morales A et al 2010. Oxidative stess and altered mitochondrial function in neurodegerative diseases: lessons from mouse models. CNS & Neurol Disorde3rs-Drug Targets 9, 439-454.
16. File S E, Fellow S., 1985. The effects of triazolobenzodiazepines in two animal tests of anxiety and in the holeboard. Br J Pharmacol 86, 729-735.
17. Finkel T, Holbrook N 2000. Oxidants, oxidative stress and the biology of ageing. Nature 408, 1313-17.
18. Franceschi C and Campisi J 2014. Chronic inflammation (inflammaging) and its potential contribution to age-related diseases. J Gerontol A Biol Sci Med Sci 69 (Sunni 1), S4-S9.
19. Franceschi C, Capri M, Monti D et al 2007. Inflammaging and anti-inflammaging: a systemic perspective on aging and longevity emrged from studies on humans. Mech Aging Develop 128, 92-105.
20. Goossens V, Grooten J, De Vos K, Fiers W 1995. Direct evidence for tumor necrosis factor-induced mitochondrial reactive oxygen intermediates and their involvement in cytotoxicity. Proc Natl Acad Sci USA 92, 8115-19.
21. Henchcliffe C, Beal M F 2008. Mitochondrial biology and oxidative stress in Parkinson disease pathogenesis. Nature Clin Practice Neurol 4, 600-609.
22. Henneka M T, Carson M J, Khoury J et al, 2015. Neuroinflammation in Alzheimer's disease. Lancet Neurol 14, 388-405.
23. Heppner F L, Ransohoff R M, Becher B, 2015. Immune attack: the role of inflammation in Alzheimer disease. Nature Rev Neurosc 16, 358-372.
24. Hui, K. M., Huen, M. S., Wang, H. Y., Zheng, H., Sigel, E., Baur, R., Ren, H., Li, Z. W., Wong, J. T., Xue, H., 2002. Anxiolytic effect of wogonin, a benzodiazepine receptor ligand isolated from Scutellaria baicalensis Georgi. Biochemical pharmacology 64, 1415-1424.
25. Jaturapatporn D, Isaac M G, McCleery J, Tabet N, 2012. Aspirin, steroidal and non-steroidal anti-inflammatory drugs for the treatment of Alzheimer's disease. Cochrane Database Syst Rev 2: CD006378. doi: 10.1002/14651858.pub2
26. Ji, W., Wang, W., Liu, W., 2007. Effects of n-Butanol Extract of Flos Albiziae on Sleep Time and Acute Toxicity in Mice. Chinese Archives of Traditional Chinese Medicine 25, 242-244.
27. Jiang W Y (2005) Therapeutic wisdom in traditional Chinese medicine: a perspective from modern science. Trends Pharmacol Sci 26(11): 558-563.
28. Jordens R G, Berry M D, Gillot C, Boulton A A 1999. Prolongation of life in an experimental model of aging in Drosophila melanogaster. Neurochem Res 24, 227-233.
29. Kalueff, A. V., Tuohimaa, P., 2004. Experimental modeling of anxiety and depression. Acta Neurobiol Exp (Wars) 64, 439-448.
30. Kang, T. H., Jeong, S. J., Kim, N. Y., Higuchi, R., Kim, Y. C., 2000. Sedative activity of two flavonol glycosides isolated from the flowers of Albizzia julibrissin Durazz. J Ethnopharmacol 71, 321-323.
31. Karl T, Pabst R, and Von HOrsten S, 2003. Behavioral phenotyping of mice in pharmacological and toxicological research. Exp Toxic Pathol 55, 69-83.
32. Leung, W. C., Zheng, H., Huen, M., Law, S. L., Xue, H., 2003. Anxiolytic-like action of orally administered dl-tetrahydropalmatine in elevated plus-maze. Prog Neuropsychopharmacol Biol Psychiatry 27, 775-779.
33. Li, Z., Zhang, M., Mao, Z., Fan, G., 2006. Studies on fraction with antidepressant activity from the flower of Albizzia Julibrissin Durazz. LiShiZhen Medicine and Materia Medica Research 8.
34. Liao, J. F., Jan, Y. M., Huang, S. Y., Wang, H. H., Yu, L. L., Chen, C. F., 1995. Evaluation with receptor binding assay on the water extracts of ten CNS-active Chinese herbal drugs. Proc Natl Sci Counc Repub China B 19, 151-158.
35. Liu, Y. L., Yan, L. D., Zhou, P. L., Wu, C. F., Gong, Z. H., 2009. Levo-tetrahydropalmatine attenuates oxycodone-induced conditioned place preference in rats. European journal of pharmacology 602, 321-327.
36. Lovell M A, Ehmann W D, Butler S M, Markesbery W R 1995. Elevated thiobarbituric acid-reactive substances and antioxidant acrtivity in the brain in Alzheimer's disease. Neurology 45, 1594-1601.
37. Mantsch, J. R., Li, S. J., Risinger, R., Awad, S., Katz, E., Baker, D. A., Yang, Z., 2007. Levo-tetrahydropalmatine attenuates cocaine self-administration and cocaine-induced reinstatement in rats. Psychopharmacology 192, 581-591.
38. Mendez, M F 2006. The accurate diagnosis of early-onset dementia. Internat J Psychiatry Med 36, 401-412.
39. Minciullo P L, Catalano A, Mandraffino G et al 2016. Inflammging and anti-inflammaging: the role of cytokines in extreme longevity. Archivum Immunol Therap Experimentalis 64, 111-126.
40. Moosmann B, Behl C 2002. Antioxidants as treatment for neurodegenerative disorders. Expert Opin Investig Drugs 11, 1407-1435.
41. Nazari-Serenjeh F, Rezayof A, Zarrindast M R., 2011. Functional correlation between GABAergic and dopaminergic systems of dorsal hippocampus and ventral tegmental area in passive avoidance learning in rats. Neuroscience 196, 104-114.
42. NIHSeniorHealth 2012: Parkinson's Disease-Symptoms and Diagnosis.

43. Nunomura A, Perry G, Aliev G et al 2001. Oxidative damage is the earliest event in Alzheimer disease. J Neuropathol Exp Neurol 60, 759-767.
44. Ohkawa H, Ohishi N, Yagi K 1979. Assay for lipid peroxides in anuimal tissues by thiobarbituric acid reaction. Anal Biochem 95, 351-358.
45. Patel N S, Paris D, Mathura V et al 2005. Inflammoatry cytokine levels correlate with amyloid load in transgenic mouse models of Alzheimer's disease. J Neuroinflammation 2:9, doi:10.1186/1742-2094-2-9.
46. Perry G, Cash A D, Smith M A 2002; Alzheimer's disease and oxidative stress. J Biomed Biotech 2:3, 120-123.
47. Prasad K N, Cole W C, Hovland A R et al 1999. Multiple antioxidants in the prevention and treatment of neurodegenerative disease: analysis of biological rationale. Curr Opin Neurol 12, 761-770.
48. Pryor W A 1989. On the detection of lipid hydroperoxides in biological samples. Free Radical Biol Med 7, 177-178.
49. Qiu J (2007). 'Back to the future' for Chinese herbal medicines. Nat Rev Drug Discov 6(7): 506-507.
50. Reagan-Shaw S, Nihal, M, Ahmad, N 2016. Dose translation from animal to human studies revisited. FASEB J 22, 659-661.
51. Ross J, Sharama S, Winston J et al, 2013. CHF5074 reduces biomarkers of neuroinflammation in patients with mild cognitive impairment: a 12-week double-blind palcebo-controlled study. Cur Alzheimer Res 10, 742-753.
52. Schroeter M L, Stein T, Maslowski N, Neumann, J 2009. Neural correlates of Alzheimer's disease and mild cognitive impairment: a systematic and quantitative meta-analysis involving 1,351 patients. Neuroimage 47, 1196-1206.
53. Shao S, Xu X, Ma D, Xue C, Fu J (2002) Chai hu jiang huang dui xiao bai shu shi yan xing gao zhi xue zheng de yu fang zuo yong. Acta Chinese Medicine and Pharmacology 30(4): 59-60.
54. Tanila H 2012. Wading pools, fading memories-place navigation in transgenic mouse models of Alzheimer's disease. Front Aging Neurosci 4: 11. doi: 10.3389/fnagi.2012.00011
55. Tarkowski E, Andreasen N, Tarkowski A, Blennow K (2003). Intrathecal inflammation precedes development of Alzheimer's disease. J Neurol Neurosurg Psychiatry 74, 1200-05.
56. Treit, D., Menard, J., Royan, C. 1993. Anxiogenic stimuli in the elevated plus-maze. Pharmacology, biochemistry, and behavior 44, 463-469.
57. von Bohlen and Halbach O, Zacher C, Gass P, Unsicker K, 2006. Age-related alterations in hippocampal spines and deficiencies in spatial memory in mice. J Neurosci Res 83, 525-531.
58. Wing Y K 2001. Herbal treatment of insomnia. Hong Kong Med J 7(4): 392-402.
59. Wolbers T, Dudchenko P A, Wood E R 2014. Spatial memory-a unique window into healthy and pathological aging. Front Aging Neurosci 6:35. doi: 10.3389/fnagi.2014.00035
60. Wang L, Zhou G B, Liu P, Song J H, Liang Y, Yan X J, Xu F, Wang B S, Mao J H, Shen Z X, Chen S J, Chen Z (2008) Dissection of mechanisms of Chinese medicinal formula Realgar-Indigo naturalis as an effective treatment for promyelocytic leukemia. Proc Natl Acad Sci USA 10: 4826-4831.
61. Xie Z F, Huang X K ed. 1991. Dictionary of Traditional Chinese Medicine. Beijing Medical College. Commercial Press, Hong Kong.
62. Xu, S. X., Yu, L. P., Han, Y. R., Chen, Y., Jin, G. Z., 1989. Effects of tetrahydroprotoberberines on dopamine receptor subtypes in brain. Acta Pharmacologica Sinica 10, 104-110.
63. Xue, H. and Wong, J. T., 2008. The Erhuhuanteng Chinese herbal decoction. China Patent ZL200410069787.3.
64. Yuan, C. S., Mehendale, S. R., Wang, C. Z., Aung, H. H., Jiang, T., Guan, X., Shoyama, Y., 2004. Effects of *Corydalis yanhusuo* and *Angelicae dahuricae* on cold pressor-induced pain in humans: a controlled trial. J Clin Pharmacol 44, 1323-1327.
65. Yue, K., Ma, B., Ru, Q., Chen, L., Gan, Y., Wang, D., Jin, G., Li, C., 2012. The dopamine receptor antagonist levo-tetrahydropalmatine attenuates heroin self-administration and heroin-induced reinstatement in rats. Pharm Biochem Behavior 102, 1-5.
66. Zhu J, Mu X, Zeng J, Xu C, Liu J, Zhang M, Li C, Chen J, Li T, Wang Y 2014. Ginsenoside Rg1 prevents cognitive impairment and hippocampus senescence in a rat model of D-galactose-induced aging. PLoS One 9(6): e101291.

What is claimed is:

1. A composition comprising active ingredients that consist essentially of active ingredients of Radix *Bupleurum chinense* DC, Rhizoma *Corydalis yanhusuo* WT Wang, and Caulis *Polygonum multiflorum* Thunb in an amount effective for reducing the effect of aging, treating Alzheimer's disease and/or treating Parkinson's disease in a subject in need thereof, wherein Radix *Bupleurum chinense* DC, Rhizoma *Corydalis yanhusuo* WT Wang, and Caulis *Polygonum multiflorum* Thunb are present in the composition in a weight ratio of about 1.4:1:1.

2. A composition comprising active ingredients that consist essentially of active ingredients of Radix *Bupleurum chinense* DC, Rhizoma *Corydalis yanhusuo* WT Wang, and Flos *Albizia julibrissin* Durazz in an amount effective for reducing the effect of aging, treating anxiety, inducing sleep, treating Alzheimer's disease and/or treating Parkinson's disease in a subject in need thereof, wherein Radix *Bupleurum chinense* DC, Rhizoma *Corydalis yanhusuo* WT Wang, and Flos *Albizia julibrissin* Durazz are present in the composition in a weight ratio of about 1.4:1:1.

3. A composition comprising active ingredients that consist essentially of active ingredients of Radix *Bupleurum chinense* DC, Caulis *Polygonum multiflorum* Thunb, and Flos *Albizia julibrissin* Durazz in an amount effective for reducing the effect of aging, treating anxiety, treating Alzheimer's disease and/or treating Parkinson's disease in a subject in need thereof, wherein Radix *Bupleurum chinense* DC, Caulis *Polygonum multiflorum* Thunb, and Flos *Albizia julibrissin* Durazz are present in the composition in a weight ratio of about 1.4:1:1.

4. A composition comprising active ingredients that consist essentially of active ingredients of Rhizoma *Corydalis yanhusuo* WT Wang, Caulis *Polygonum multiflorum* Thunb, and Flos *Albizia julibrissin* Durazz in an amount effective for treating anxiety, and/or inducing sleep in a subject in need thereof, wherein Rhizoma *Corydalis yanhusuo* WT Wang, Caulis *Polygonum multiflorum* Thunb, and Flos *Albizia julibrissin* Durazz are present in the composition in a weight ratio of about 1:1:1.

5. A composition comprising active ingredients that consist essentially of active ingredients of Radix *Bupleurum chinense* DC and Rhizoma *Corydalis yanhusuo* WT Wang in an amount effective for reducing the effect of aging, treating Alzheimer's disease and/or treating Parkinson's disease in a subject in need thereof, wherein Radix *Bupleurum chinense* DC and Rhizoma *Corydalis yanhusuo* WT Wang are present in the composition in a weight ratio of about 1.4:1.

6. A composition comprising active ingredients that consist essentially of active ingredients of Radix *Bupleurum chinense* DC and Caulis *Polygonum multiflorum* Thunb in an amount effective for reducing the effect of aging, treating Alzheimer's disease and/or treating Parkinson's disease in a subject in need thereof, wherein Radix *Bupleurum chinense* DC and Caulis *Polygonum multiflorum* Thunb are present in the composition in a weight ratio of about 1.4:1.

7. A composition comprising active ingredients that consist essentially of active ingredients of Radix *Bupleurum chinense* DC and Flos *Albizia julibrissin* Durazz in an amount effective for treating anxiety in a subject in need thereof, wherein Radix *Bupleurum chinense* DC and Flos *Albizia julibrissin* Durazz are present in the composition in a weight ratio of about 1.4:1.

8. A composition comprising active ingredients that consist essentially of active ingredients of Rhizoma *Corydalis yanhusuo* WT Wang and Caulis *Polygonum multiflorum* Thunb in an amount effective for reducing the effect of aging, treating Alzheimer's disease and/or treating Parkinson's disease in a subject in need thereof, wherein Rhizoma *Corydalis yanhusuo* WT Wang and Caulis *Polygonum multiflorum* Thunb are present in the composition in a weight ratio of about 1:1.

9. A composition comprising active ingredients that consist essentially of active ingredients of Caulis *Polygonum multiflorum* Thunb and Flos *Albizia julibrissin* Durazz in an amount effective for treating anxiety, and/or inducing sleep in a subject in need thereof, wherein Caulis *Polygonum multiflorum* Thunb and Flos *Albizia julibrissin* Durazz are present in the composition in a weight ratio of about 1:1.

10. A pharmaceutical formulation or herbal supplement comprising the composition of any one of claims 1 to 9 and an excipient.

11. A method of reducing the effect of aging, treating Alzheimer's disease and/or treating Parkinson's disease, the method comprising administering to a subject in need thereof the composition of claim 1 or a pharmaceutical formulation or herbal supplement comprising the composition of claim 1 and an excipient to reduce the effect of aging, treat Alzheimer's disease and/or treat Parkinson's disease.

12. A method of reducing the effect of aging, treating anxiety, inducing sleep, treating Alzheimer's disease and/or treating Parkinson's disease, the method comprising administering to a subject in need thereof the composition of claim 2 or a pharmaceutical formulation or herbal supplement comprising the composition of claim 2 and an excipient to reduce the effect of aging, treat anxiety, induce sleep, treat Alzheimer's disease and/or treat Parkinson's disease.

13. A method of reducing the effect of aging, treating anxiety, treating Alzheimer's disease and/or treating Parkinson's disease, the method comprising administering to a subject in need thereof the composition of claim 3 or a pharmaceutical formulation or herbal supplement comprising the composition of claim 3 and an excipient to reduce the effect of aging, treat anxiety, treat Alzheimer's disease and/or treat Parkinson's disease.

14. A method of treating anxiety and/or inducing sleep, the method comprising administering to a subject in need thereof the composition of claim 4 or a pharmaceutical formulation or herbal supplement comprising the composition of claim 4 and an excipient to treat anxiety and/or induce sleep.

15. A method of reducing the effect of aging, treating Alzheimer's disease and/or treating Parkinson's disease, the method comprising administering to a subject in need thereof the composition of claim 5 or a pharmaceutical formulation or herbal supplement comprising the composition of claim 5 and an excipient to reduce the effect of aging, treat Alzheimer's disease and/or treat Parkinson's disease.

16. A method of reducing the effect of aging, treating Alzheimer's disease and/or treating Parkinson's disease, the method comprising administering to a subject in need thereof the composition of claim 6 or a pharmaceutical formulation or herbal supplement comprising the composition of claim 6 and an excipient to reduce the effect of aging, treat Alzheimer's disease and/or treat Parkinson's disease.

17. A method of treating anxiety, the method comprising administering to a subject in need thereof the composition of claim 7 or a pharmaceutical formulation or herbal supplement comprising the composition of claim 7 and an excipient to treat anxiety.

18. A method of reducing the effect of aging, treating Alzheimer's disease and/or treating Parkinson's disease, the method comprising administering to a subject in need thereof the composition of claim 8 or a pharmaceutical formulation or herbal supplement comprising the composition of claim 8 and an excipient to reduce the effect of aging, treat Alzheimer's disease and/or treat Parkinson's disease.

19. A method of treating anxiety and/or inducing sleep, the method comprising administering to a subject in need thereof the composition of claim 9 or a pharmaceutical formulation or herbal supplement comprising the composition of claim 9 and an excipient to treat anxiety and/or induce sleep.

20. A method of reducing the effect of aging, treating Alzheimer's disease and/or treating Parkinson's disease, the method comprising administering to a subject in need thereof a composition comprising active ingredients that consist essentially of active ingredients of Radix *Bupleurum chinense* DC, Rhizoma *Corydalis yanhusuo* WT Wang, Caulis *Polygonum multiflorum* Thunb, and Flos *Albizia julibrissin* Durazz in an amount effective for reducing the effect of aging, treating Alzheimer's disease and/or treating Parkinson's disease, wherein Radix *Bupleurum chinense* DC, Rhizoma *Corydalis yanhusuo* WT Wang, Caulis *Polygonum multiflorum* Thunb, and Flos *Albizia julibrissin* Durazz are present in the composition in a weight ratio of about 1.4:1:1:1; or a pharmaceutical formulation or herbal supplement comprising the composition and an excipient to reduce the effect of aging, treat Alzheimer's disease and/or treat Parkinson's disease.

* * * * *